United States Patent
Chang et al.

(10) Patent No.: US 11,446,654 B2
(45) Date of Patent: Sep. 20, 2022

(54) SUBSTRATE WITH CHANNELS FOR CONTROLLED FLUID FLOW

(71) Applicant: Quidel Corporation, San Diego, CA (US)

(72) Inventors: Samantha Chang, San Marcos, CA (US); Jason McClure, San Diego, CA (US); Robert Reed, Carlsbad, CA (US); Irene Sinn Blandy, San Diego, CA (US); Robert Weiller, Encinitas, CA (US); Christian Bobritchi, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 177 days.

(21) Appl. No.: 15/893,375

(22) Filed: Feb. 9, 2018

(65) Prior Publication Data
US 2018/0229232 A1  Aug. 16, 2018

Related U.S. Application Data

(60) Provisional application No. 62/598,947, filed on Dec. 14, 2017, provisional application No. 62/472,182, filed on Mar. 16, 2017, provisional application No. 62/457,660, filed on Feb. 10, 2017.

(51) Int. Cl.
*B01L 3/00* (2006.01)
*G01N 33/558* (2006.01)
(Continued)

(52) U.S. Cl.
CPC ......... *B01L 3/5023* (2013.01); *B01L 3/5027* (2013.01); *G01N 33/54386* (2013.01);
(Continued)

(58) Field of Classification Search
USPC ......... 436/10, 180, 501, 517, 518, 519, 531, 436/536; 422/68.1, 73, 502–504
See application file for complete search history.

(56) References Cited

U.S. PATENT DOCUMENTS 5,356,782 A  10/1994  Moorman et al.
5,705,397 A   1/1998  Bunce
(Continued)

FOREIGN PATENT DOCUMENTS

EP  0516095 A2  12/1992
EP  1096256 A1   5/2001
(Continued)

OTHER PUBLICATIONS

International Search Report from International Application No. PCT/US2018/017584, 5pgs, dated May 3, 2018.
(Continued)

*Primary Examiner* — Dean Kwak
(74) *Attorney, Agent, or Firm* — McDermott Will and Emery LLP; Judy Mohr; Brett A. Schweers

(57) ABSTRACT

A substrate structured to define thereon a fluid flow channel and/or a fluid control feature is described. The substrate may additionally comprise a capture zone and/or a test zone, for use as a test strip for determining presence or absence of an analyte of interest, such as an infectious agent or a biomarker. Reagents are deposited in the capture zone and/or test zone as an array of drops.

11 Claims, 24 Drawing Sheets

(51) Int. Cl.
*G01N 33/543* (2006.01)
*G01N 33/569* (2006.01)

(52) U.S. Cl.
CPC .... *G01N 33/558* (2013.01); *B01L 2300/0858* (2013.01); *B01L 2300/0861* (2013.01); *B01L 2400/082* (2013.01); *G01N 33/569* (2013.01)

(56) References Cited

U.S. PATENT DOCUMENTS

| | | | |
|---|---|---|---|
| 6,656,745 B1 * | 12/2003 | Cole | G01N 33/54386 |
| | | | 422/408 |
| 7,858,396 B2 | 12/2010 | Corstjens et al. | |
| 8,273,307 B2 | 9/2012 | Eickhoff et al. | |
| 8,486,717 B2 | 7/2013 | O'Farrell et al. | |
| 8,614,100 B2 | 12/2013 | Nordhoff et al. | |
| 8,895,293 B2 | 11/2014 | Kanaley et al. | |
| 9,017,995 B2 | 4/2015 | Pflanz et al. | |
| 9,851,366 B2 | 12/2017 | O'Farrell | |
| 9,874,576 B2 | 1/2018 | O'Farrell | |
| 2005/0250141 A1 | 11/2005 | Lambert et al. | |
| 2006/0039829 A1 | 2/2006 | Suk et al. | |
| 2006/0246600 A1 | 11/2006 | Yang et al. | |
| 2008/0131977 A1 | 6/2008 | Rosenstein et al. | |
| 2010/0159599 A1 | 6/2010 | Song et al. | |
| 2010/0159611 A1 | 6/2010 | Song et al. | |
| 2011/0136259 A1 | 6/2011 | Love et al. | |
| 2012/0015368 A1 * | 1/2012 | Del Galdo | C12Q 1/6883 |
| | | | 435/6.12 |
| 2014/0213483 A1 | 7/2014 | Radelof et al. | |
| 2015/0111216 A1 * | 4/2015 | Delahunt | G02B 21/34 |
| | | | 435/6.15 |
| 2015/0119296 A1 | 4/2015 | Tisone et al. | |
| 2017/0248573 A1 * | 8/2017 | Sullivan | B01L 3/5027 |

FOREIGN PATENT DOCUMENTS

| | | |
|---|---|---|
| EP | 2955519 A1 | 12/2015 |
| EP | 3171169 A1 | 5/2017 |
| JP | H04-351962 A | 12/1992 |
| JP | 3066540 B2 | 7/2000 |
| JP | 2000-321277 A | 11/2000 |
| JP | 3451088 B2 | 9/2003 |
| JP | 2005-291744 A | 10/2005 |
| JP | 2007-114097 A | 5/2007 |
| JP | 2007-523355 A | 8/2007 |
| JP | 2009-250763 A | 10/2009 |
| JP | 2013-148584 A | 8/2013 |
| JP | 2016-217847 A | 12/2016 |
| WO | WO 1993/024231 A1 | 12/1993 |
| WO | WO 1998/039657 A1 | 9/1998 |
| WO | WO 2006/118622 A1 | 11/2006 |
| WO | WO 2010/070468 A2 | 6/2010 |
| WO | WO 2015/188906 A1 | 12/2015 |
| WO | WO 2016/049221 A1 | 3/2016 |
| WO | WO 2017/084728 A1 | 5/2017 |

OTHER PUBLICATIONS

Costa et al., "A low cost, safe, disposable, rapid and self-sustainable paper-based platform for diagnostic testing: lab-on-paper", Nanotechnology, vol. 25, No. 9, pp. 094006, 1-12 (2014).

He et al., "Laser-based patterning for fluidic devices in nitrocellulose", Biomicrofluidics, vol. 9, No. 2, pp. 026503, 1-10 (2015).

Spicar-Mihalic et al., "$CO_2$ laser cutting and ablative etching for the fabrication of paper-based devices", J. Micromech. Microeng., vol. 23, No. 6, pp. 067003, 1-6 (2013).

Yetisen et al., "Paper-based microfluidic point-of-care diagnostic devices", Lab Chip, vol. 13, pp. 2210-2251 (2013).

* cited by examiner

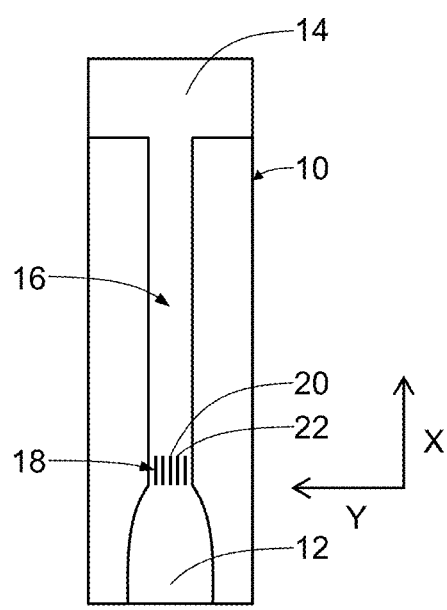 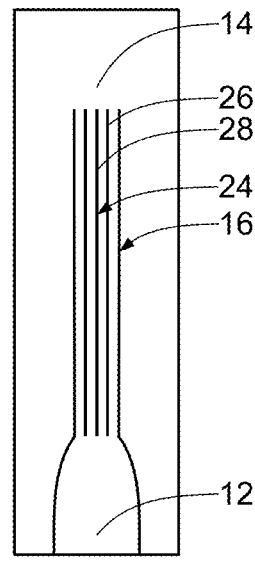 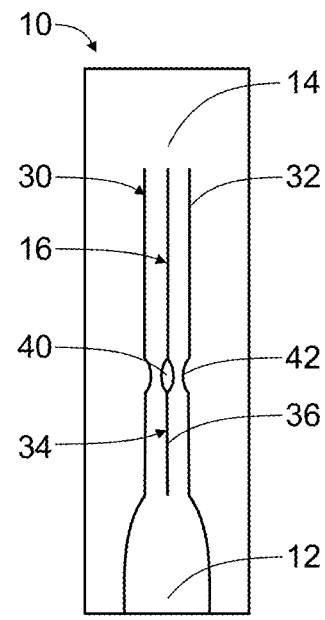
FIG. 1A  FIG. 1B  FIG. 1C
   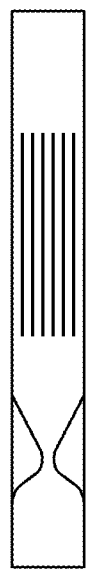
FIG. 1D  FIG. 1E  FIG. 1F  FIG. 1G
FIG. 1H  FIG. 1I  FIG. 1J

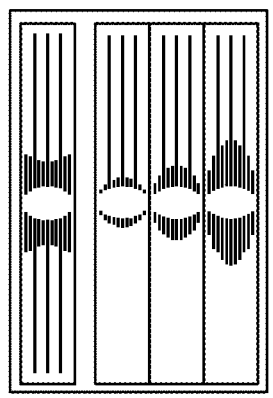
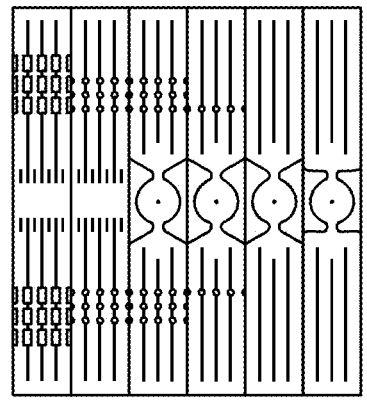
FIG. 3       FIG. 4
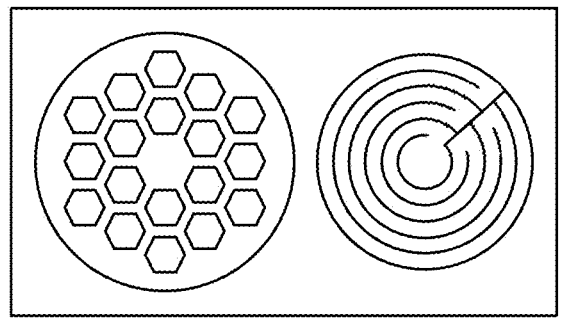
FIG. 5
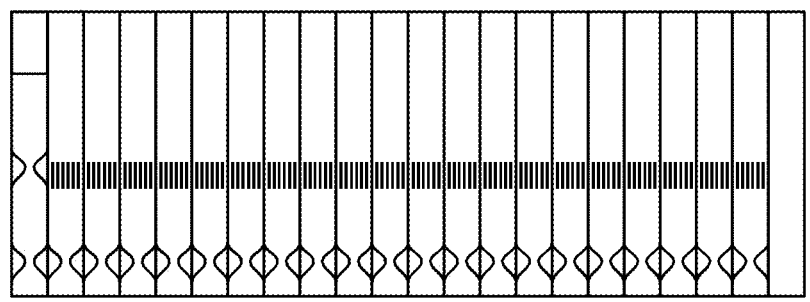
FIG. 6

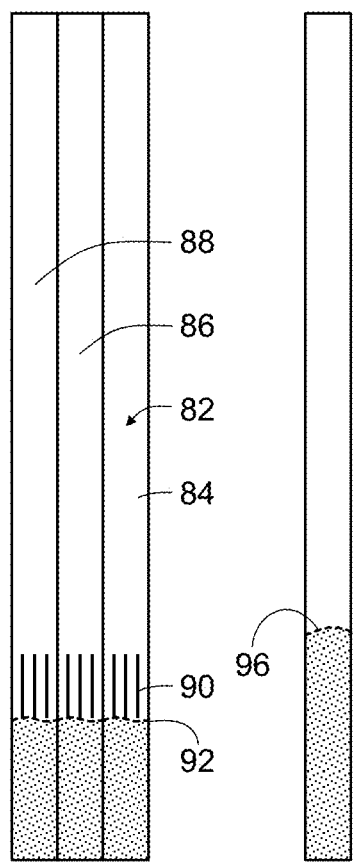
FIG. 10A  FIG. 10B
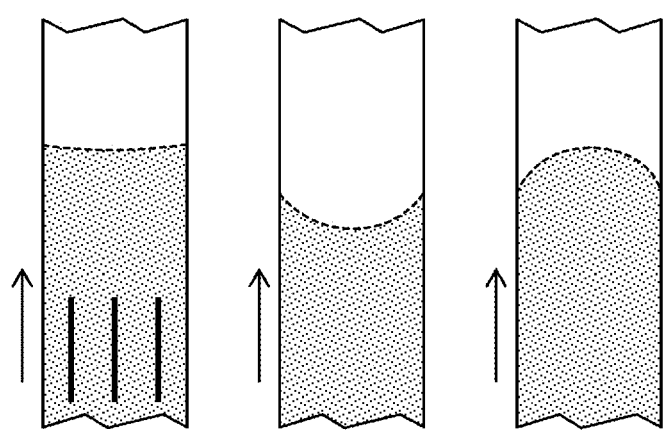
FIG. 11A  FIG. 11B  FIG. 11C

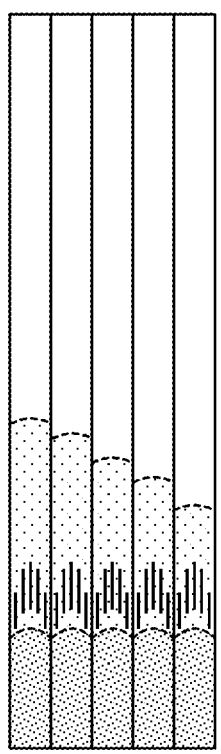 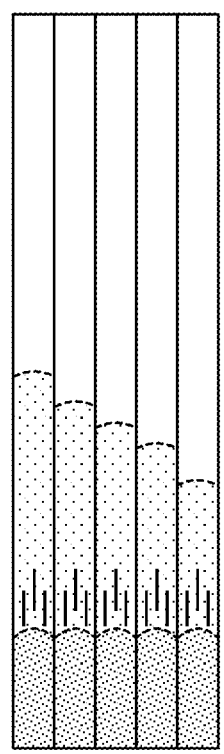
FIG. 12A  FIG. 12B
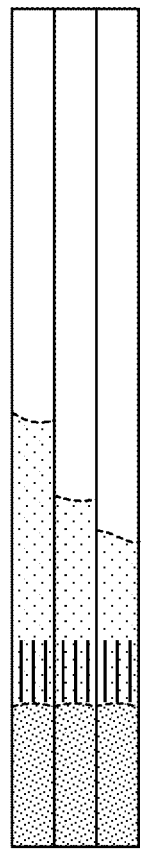 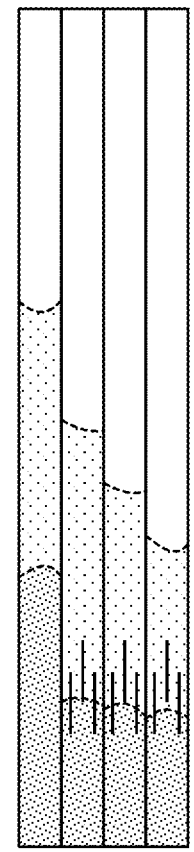 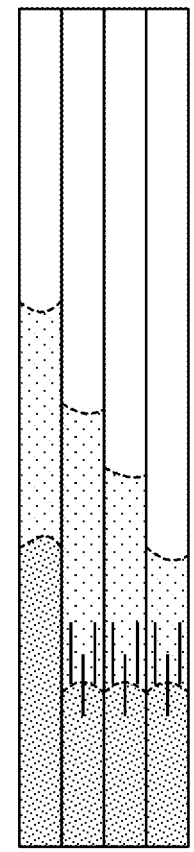
FIG. 13A  FIG. 13B  FIG. 13C

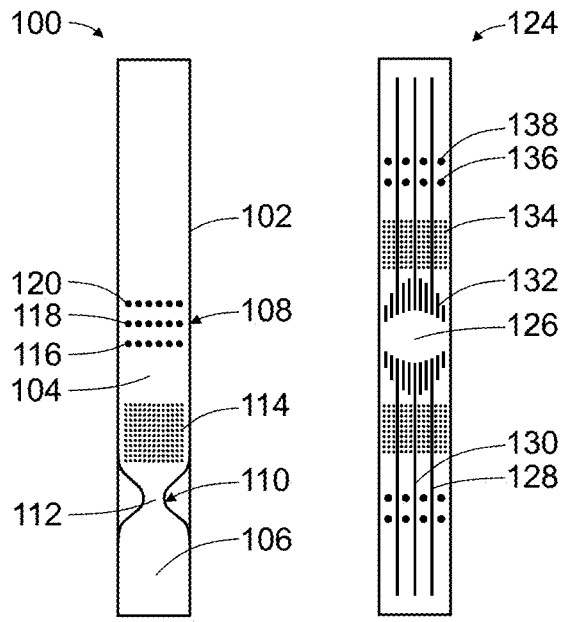
FIG. 14A   FIG. 14B
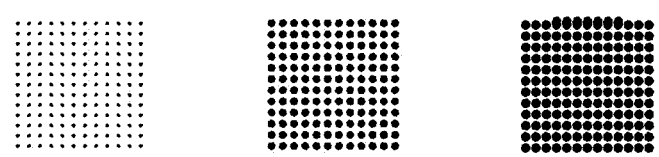
FIG. 15A   FIG. 15B   FIG. 15C
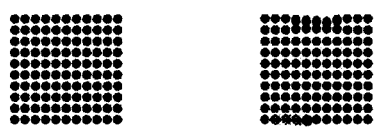
FIG. 16A   FIG. 16B

10 µL droplet on a nitrocellulose substrate direct cast on a hydrophobic backing 10 µL droplet on a nitrocellulose attached to a hydrophobic backing by an adhesive

SUBSTRATE WITH CHANNELS FOR CONTROLLED FLUID FLOW

CROSS-REFERENCE TO RELATED APPLICATIONS

This application claims the benefit of U.S. Provisional Application No. 62/457,660, filed Feb. 10, 2017, of U.S. Provisional Application No. 62/472,182, filed Mar. 16, 2017, and of U.S. Provisional Application No. 62/598,947, filed Dec. 14, 2017, each of which is incorporated herein by reference in its entirety.

TECHNICAL FIELD

The subject matter described herein relates to substrates that have a fluid flow channel and a fluid control feature created by exposure to a laser beam, where the fluid control feature is configured to control the rate of fluid flow and/or uniformity of fluid flow. The substrates find use, for example, in lateral flow assays to detect and/or discriminate a species of interest in a fluid sample.

BACKGROUND

Lateral flow assays are an established technology that can be adapted for a variety of testing applications for sensors, diagnostics, and indicators. Lateral flow assays typically consist of a material or substrate to transport a fluid sample of interest from the point of application (e.g. the sample collection zone) to the detection zone(s) via passive capillary action. For example, rapid lateral flow immunoassays test devices are used in both the clinical and the home settings. These devices are used to test for a variety of analytes, such as hormones, proteins, urine or plasma components and the like. These devices generally comprise a lateral flow test strip, such as nitrocellulose or filter paper, a sample application area, test results area and an analyte specific binding reagent that is bound to some kind of detectable label, such as a colored particle (such as a europium bead), a fluorescent or luminescent tag, or an enzyme detection system. The simplicity of such devices is a factor in maintaining their use in the marketplace. Because the method of fluid transport is passive, the rate of flow as well as the specific flow path is largely fixed by the viscosity of the liquid sample, the substrate material, and the chemical nature of any coatings that may be applied (e.g., hydrophilic or hydrophobic). It would be advantageous to alter the flow rate or control the uniformity of fluid flow without adding extra components or materials to the substrate. An approach to modify and regulate the flow rate and flow uniformity of a fluid sample deposited on a substrate in a lateral flow assay is desired.

BRIEF SUMMARY

The following aspects and embodiments thereof described and illustrated below are meant to be exemplary and illustrative, not limiting in scope.

In one aspect, a substrate is provided. The substrate comprises a sample receiving zone; a destination zone; a fluid pathway extending from the sample receiving zone and the destination zone; and a fluid control feature created on the substrate to control (i) rate of a fluid flow across the destination zone, and/or (ii) uniformity of rate of flow of a leading edge of a moving fluid across the destination zone.

In another aspect, a device comprising a substrate is provided. The substrate comprises a sample receiving zone, a destination zone, a fluid pathway extending from the sample receiving zone and the destination zone, and a fluid control feature positioned on the substrate to control (i) rate of a fluid flow across the destination zone, and/or (ii) uniformity of rate of flow of a leading edge of a moving fluid across the destination zone.

In one embodiment, the fluid control feature is in a flow rate control zone that, in one embodiment, is disposed between the sample receiving zone and the destination zone.

In one embodiment, the destination zone is a label zone.

In one embodiment, the flow rate control zone is disposed between the sample receiving zone and the label zone.

In another embodiment, the substrate is nitrocellulose. In another embodiment, the substrate is a laminate of a nitrocellulose layer and a hydrophobic support layer.

In one embodiment, the nitrocellulose is not treated with or impregnated with a polymer, including a photo-polymer, prior to exposure to a laser to create the fluid control feature and/or the side walls of a fluid flow channel.

In another aspect, an immunoassay device comprising a substrate or a device as described herein is provided.

In still another aspect, a device comprising a substrate having a thickness/and a first fluid flow channel on the substrate is provided. The first fluid flow channel comprises a fluid flow path on or within the substrate and is defined and bounded by opposing substrate-free side walls or channels, that, in one embodiment, are created by exposure of the substrate to a laser. The opposing substrate-free side channels are impermeable to fluid flow. A first fluid control feature is disposed on the substrate to control (i) rate of a fluid flow in the first fluid flow channel and/or (ii) uniformity of rate of flow of a leading edge of a moving fluid in the first fluid flow channel.

In one embodiment, the device comprises a second fluid flow channel defined on or within the substrate by opposing, substrate-free side walls or channels that are impermeable to fluid flow.

In one embodiment, the second fluid flow channel comprises a second fluid flow control feature having a shape and a position on the substrate to control (i) rate of a fluid flow in the second fluid flow channel and/or (ii) uniformity of rate of flow of a leading edge of a moving fluid in the second fluid flow channel.

In one embodiment, the fluid flow control feature and/or the opposing substrate-free side channels have a depth equal to substrate thickness 1. In one embodiment, the substrate is a nitrocellulose substrate attached to a support layer or second substrate that is a hydrophobic material to form a laminate.

In one embodiment, the second fluid flow channel has a fluid flow path parallel to the first fluid flow path in the first fluid flow channel, wherein fluid in the first channel is isolated from fluid in the second channel by a substrate-free side channel, which in one embodiment is a common substrate-free side channel.

In one embodiment, the second fluid flow channel has a fluid flow path that is in a direction opposite from the fluid flow path in the first fluid flow channel.

In one embodiment, the first fluid flow channel is circular and defines a circular fluid flow path.

In yet another aspect, an immunoassay device is provided. The device comprises a single, integral substrate and a single, sample receiving zone on the substrate, the sample receiving zone positioned to distribute at least a portion of a sample deposited thereon to a fluid flow path comprising a label zone and a capture zone downstream of the label zone. The label zone, the capture zone, or both the label zone and the capture zone are comprised of an n×m array of discrete dots, where n is greater than or equal to one (1) and m is greater than or equal to zero (0), wherein when m is greater than zero each dot in the n×m array is separated from an adjacent dot by a distance x, and wherein each dot is comprised of a reagent comprising a binding member.

In yet another aspect, an immunoassay device is provided. The device comprises a single, integral substrate and a single sample receiving zone on the substrate. The sample receiving zone is positioned to distribute a portion of a sample deposited thereon to each of a plurality of discrete fluid flow paths, each fluid flow path comprising a label zone and a capture zone downstream of the label zone. The label zone, the capture zone, or both the label zone and the capture zone are comprised of an n×m array of discrete dots, where n is greater than or equal to one (1) and m is greater than or equal to zero (0), wherein when m is greater than zero each dot in the n×m array is separated from an adjacent dot by a distance x, and wherein each dot is comprised of a reagent comprising a binding member.

In one embodiment, each fluid flow path in the plurality of fluid flow paths is separated from an adjacent fluid flow path by a physical barrier formed by laser etching of the substrate. In one embodiment, the physical barrier is a gap corresponding to a region of substrate-free channel. In another embodiment, each fluid flow path in the plurality of fluid flow paths is separated from an adjacent fluid flow path by a hydrophobic and/or physical barrier formed by laser etching of the substrate. In one embodiment, the hydrophobic barrier is a hydrophobic support layer laminated to the substrate, the barrier corresponding to a substrate-free channel or gap of substrate to expose the hydrophobic support layer.

In another embodiment, the plurality of fluid flow paths comprises between 2-50 fluid flow paths. In another embodiment, the plurality of fluid flow paths comprises between 3-50, 2-12 or 2-8 or 2-6 fluid flow paths.

In another embodiment, the capture zone of each fluid flow path is within a single optical window for inspection by an instrument.

In still another embodiment, the sample receiving zone dispenses sample to each channel in essentially equal amounts and at essentially equal rates.

In yet another embodiment, the capture zone in each fluid flow path in the plurality of fluid flow paths comprises an immobilized species that directly or indirectly binds antibody against the infectious agent, an antigen, or a marker for an antigen present in a liquid sample deposited in the sample receiving zone. In another embodiment, the capture zone comprises a species that binds a conjugate comprised of a detectable species and an antibody against the infectious agent, antigen, or a marker for an antigen present in the liquid sample.

In one embodiment, the detectable species comprises an antibody.

In one embodiment, the detectable species comprises an optically detectable label.

In one embodiment, the optically detectable label is a fluorescent or chemiluminescent marker.

In one embodiment, the optically detectable label is a non-visually optically detectable label.

In one embodiment, the detectable species is a europium bead.

In another aspect, an immunoassay device for detection of a plurality of analytes in a sample is provided. The device comprises a substrate comprising a common zone configured to receive a liquid sample, to a plurality of channels extending from the common zone, each channel in the plurality of channels having a discrete fluid flow and positioned to receive a portion of the sample deposited in the common zone, each fluid flow path comprising an associated label zone comprising a mobilizable, detectable species that binds to an analyte, if present, in the portion of the sample distributed to the channel, and a capture zone in each fluid flow path positioned downstream of the label zone, the capture zone comprising an immobilized species with direct or indirect binding affinity for the mobilizable detectable species. Each channel with its fluid flow path originates from the common zone (which may be in some embodiments a sample receiving zone) and each fluid flow path is separate and distinct from that of an adjacent channel to minimize, and preferably substantially eliminate cross-contamination between adjacent channels. Each channel comprises in its fluid flow path a fluid control feature created by exposure of the substrate to a laser.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE DRAWINGS

FIGS. 1A-1L illustrate substrates with fluid flow channels comprising a fluid control feature created via exposure of the substrate to a laser beam;

FIGS. 3-9 show substrates with laser-etched fluid flow patterns, including fluid control features, according to some embodiments;

FIG. 10A is an artist's rendering of a photograph of a substrate with a laser-etched channel with a laser-etched fluid control feature configured to control uniformity of the leading edge of a moving fluid front in the channel;

FIG. 10B is an artist's rendering of a photograph showing the leading edge of a moving fluid front in a channel lacking a fluid control feature;

FIGS. 11A-11C illustrate an essentially uniform or flat presentation of the leading edge of the moving fluid front in a fluid flow channel (FIG. 11A) and non-uniform leading edge of moving fluid fronts (FIGS. 11B-11C);

FIGS. 12A-12B are artist's renderings of photographs of substrates with laser-etched channels with a laser-etched fluid control feature, where the fluid control feature in each channel is configured to control uniformity of the leading edge of a moving fluid front and to control rate of fluid flow in the channel;

FIG. 13A is an artist's rendering of a photograph of a substrate with a plurality of laser-etched channels, each comprising a laser-etched fluid control feature configured to control uniformity of the leading edge of a moving fluid front and to control rate of fluid flow in the channel;

FIGS. 13B-13C are artist's renderings of photographs of substrates with a plurality of laser-etched channels each comprising a laser-etched fluid control feature that do not provide the desired control of uniformity of the leading edge of a moving fluid front;

FIG. 14A is an immunoassay test strip comprising a substrate with a single channel having a fluid control feature, a label zone, and test zones;

FIG. 14B is an immunoassay test strip with 8 fluid flow channels emanating from a single sample zone, where each channel comprises a laser-etched fluid control feature, a label zone, and test and control zones;

FIGS. 15A-15C illustrate dot-arrays deposited on the substrate to form the label zone, test zone and/or control zone;

FIGS. 16A-16B illustrate deposition of dot-arrays on the substrate and control of dot pitch and positional accuracy;

FIG. 22A shows an image taken directly above a sample droplet placed on a substrate with a hydrophobic backing, and FIG. 22B shows a lateral view of the same. FIG. 22C shows an image taken directly above a sample droplet placed on a substrate with a hydrophilic backing, and FIG. 22D shows a lateral view of the same.

FIG. 30A shows the capture flow time and FIG. 30B shows the completion time.

DETAILED DESCRIPTION

I. Definitions

Figures 1K, 1L:
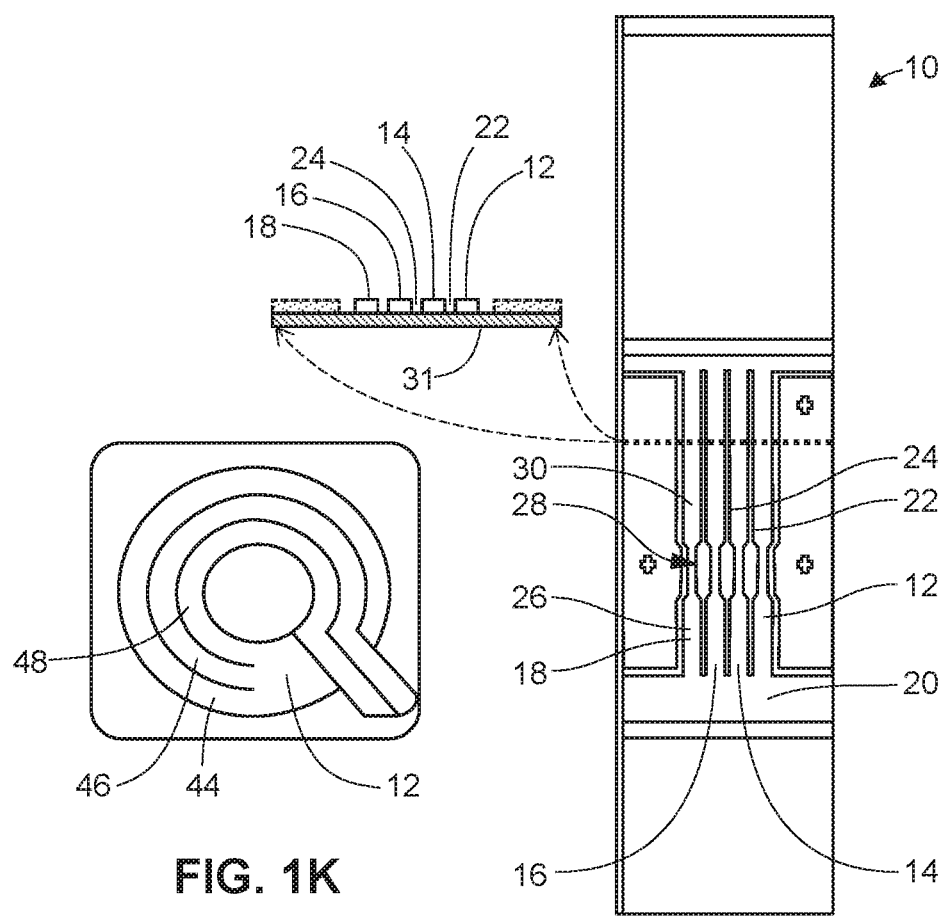

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

"Sample" is any material to be tested for the presence or amount of an analyte of interest. Preferably, a sample is a fluid sample, preferably a liquid sample. Examples of liquid samples that may be tested using a test device include bodily fluids including blood, serum, plasma, saliva, urine, ocular fluid, semen, sputum, nasal discharge and spinal fluid.

II. Substrate with Fluid Channel Comprising a Fluid Control Feature

In a first aspect, a substrate comprising a sample receiving zone and a destination zone with a fluid pathway extending from the sample receiving zone to the destination zone is provided. Created in the fluid pathway of the substrate is a fluid control feature. Examples of fluid control features configured to control (i) rate of a fluid flow across the destination zone and/or (ii) uniformity of rate of flow of a leading edge of a moving fluid across the destination zone are now described, with reference to FIGS. 1A-1L.

With initial reference to FIG. 1A, a substrate 10 comprising a sample receiving zone 12 and a destination zone 14 is illustrated. Destination zone 14 is downstream of the sample receiving zone. Extending between the zones is a fluid flow channel 16 that comprises a fluid control feature 18 created via exposure of the substrate to a laser beam, a chemical etch or a mechanical ablation means. The fluid control feature is positioned, in some embodiments, in a fluid flow rate control zone, typically disposed between a sample receiving zone and a downstream fluid flow channel or between a conjugation zone and a capture zone, described infra.

In one embodiment, the fluid control feature(s) and/or the walls, channels, barriers that define the sample receiving zone and destination zone are created in the substrate using a laser, a mechanical method or a chemical method. Structuring of the substrate using a laser is also referred to herein as laser-etching or laser-ablation. Examples of suitable lasers are given infra. In the exemplary embodiments herein, the fluid control feature(s) and the opposing barriers or side channels that define the fluid flow channels were created in the substrate via laser structuring. A skilled artisan will appreciate that a chemical etch process or a mechanical method could be used to create the fluid control feature(s) and side channels. As used herein, a "structured substrate" intends a substrate that has been exposed to a process to create one or more fluid control features and/or wall, channel, gap, or barrier that defines one or more of the fluid flow channel, the sample receiving zone and/or the destination zone by any means, including exposure to a laser, exposure to a chemical, or exposure to a mechanical process.

The substrate is a bibulous or a non-bibulous material. Suitable materials include, but are not limited to, materials derived from cellulose, such as filter paper, chromatographic paper, nitrocellulose, and cellulose acetate, as well as materials made of glass fiber, nylon, polyester, polyacrylamide, cross-linked dextran, agarose, polyacrylate, ceramics, and the like. In one embodiment, the substrate is a nitrocellulose substrate. In another embodiment, the nitrocellulose substrate is neat nitrocellulose, meaning that the nitrocellulose substrate is not treated with or impregnated with a polymer or a photo-polymer prior to exposure to a laser or chemical etch process to create the fluid control feature and/or the side walls. However, post exposure to a process to structure the substrate (e.g., laser, chemical etch, mechanical etch) to create the fluid control feature and/or the side walls the substrate may optionally be treated to modify its wetting and/or capillary flow characteristics or the characteristics of an applied sample.

In one embodiment, the substrate is a nitrocellulose substrate that is laminated to a base or support layer to form a laminate. In one embodiment, the base layer is a hydrophobic material, and in another embodiment the base layer is a hydrophilic material. A hydrophobic material is one that has a contact angle with a liquid (e.g., water) of >90 degrees. A hydrophilic material is one that has a contact angle with a liquid (e.g., water) of <90 degrees. Exemplary hydrophobic materials are, for example, adhesives, polyesters; although it will be appreciated that a polyester can be rendered hydrophilic by extruding the fibers into certain shapes or treating the fibers. Depending on the nature of the fluid sample employed, the hydrophobic or hydrophilic nature of the backing can be configured as described herein to provide a fluidic barrier which reduces or eliminates fluidic crosstalk between channels, flooding of fluidic sample into the structured (e.g., laser-etched) regions, seeping of the fluidic sample beneath the substrate, and susceptibility of sample flow rate to external forces (e.g., vibrations). In addition, adequate lamination or other forms of attachment of the substrate to the backing is important to controlling fluidic crosstalk between channels, flooding of fluidic sample into the structured (e.g., laser-etched) regions, and seeping of the fluidic sample beneath the substrate. These features of hydrophobic or hydrophilic backing and adequate lamination further provide a medium whereby sample flow is uniform along a fluid pathway.

Upon exposure of the nitrocellulose substrate to a laser, the base layer is exposed due to, for example, ablation or removal of the nitrocellulose, thus providing a substrate-free region of exposed, base layer. In one embodiment, where the base layer is a hydrophobic material, the hydrophobic material is exposed upon laser etching or ablation of the nitrocellulose substrate, and the exposed hydrophobic material forms an additional barrier to fluid flow. Laser ablation of regions on the substrate to create, for example, a fluid control feature and/or side walls or channels, can be controlled to remove the substrate material in its entirety in the laser treated region, such that the laser treated region is entirely devoid of substrate (e.g., nitrocellulose substrate), that is it is 'substrate-free'. In embodiments where the laser-etched nitrocellulose substrate is attached to a base layer, such as a hydrophobic material or a hydrophilic material, a laminate is created where the base layer is exposed to the environment of use in those regions where the substrate is ablated by laser etching.

The substrate, with or without a base layer, is exposed, in one embodiment, to a laser beam to create the fluid control feature, and in embodiments described infra, to also create the fluid flow channel. With regard to the latter, in embodiments where a multiplicity of individual, discrete channels are on a single, discrete substrate, more than one channel is created by laser-etching side channels to define the fluid flow channel. Each channel is a discrete fluid flow path with no measurable cross-talk or fluid communication with an adjacent channel, however, the multiplicity of channels generally emanate from or terminate at a common zone. The channels in the plurality (multiplicity) of channels are not in fluid communication with an adjacent channel other than via a common starting zone (e.g., a sample receiving zone) or a termination zone (e.g. a wicking zone or absorbent pad). Each channel is separated from the other by a gap where substrate material is removed-referred to as a 'substrate-free side channel'.

With continued reference to FIG. 1A, fluid control feature 18 in this embodiment is comprised of a plurality of laser-etched lines, and lines 20, 22 are representative. The laser-etched lines in the fluid control feature correspond to regions where the substrate material is ablated by exposure to the laser beam or etched by exposure to the laser beam. Thus the region of the substrate where the fluid control feature is situated consists of intact regions of substrate and regions of ablated or etched substrate that direct a fluid flowing into or within the region into the intact substrate regions. In one embodiment, the plurality of laser etched lines in a fluid control feature comprised of a plurality of essentially parallel lines comprises n lines, where n is 3, 4, 5, 6, 7, 8, 9, or 10. Each line has a proximal end and a distal end downstream of the proximal end. In one embodiment, the proximal ends of each line in the plurality are arranged such that a line drawn to intersect each proximal end is a straight line. That is, a line drawn in the y direction as indicated in FIG. 1A that intersects each proximal end of each line in the plurality is a straight line. In another embodiment, the distal ends of each line in the plurality are arranged such that a line drawn to intersect each distal end is a straight line. That is, a line drawn in the y direction as indicated in FIG. 1A that intersects each distal end of each line in the plurality is a straight line. In the fluid control feature 18 of FIG. 1A, the proximal and distal ends of each line in the plurality of lines forming the fluid control feature are arranged such that a line drawn to intersect each proximal end is a straight line and a line drawn to intersect each distal end is a straight line.

The plurality of laser etched lines forming fluid control feature 18 in FIG. 1A are positioned at the junction between sample receiving zone 12 and the beginning or upstream portion of fluid flow channel 16, this junction referred to as a fluid flow rate control zone. It is also observed that the plurality of laser etched lines forming fluid control feature 18 in FIG. 1A have a length $l_1$ that is between about 0.07-0.1 the length $l_2$ of the fluid flow channel. In other embodiments, the ratio of $l_1$ to $l_2$ is between about 0.05-1.0, between about 0.08-0.8, between about 0.1-0.5, between about 0.1-0.3, between about 0.1-0.25, or between about 0.1-0.2.

FIG. 1B shows an embodiment of a substrate similar to FIG. 1A (like reference numbers identify like features for convenience). The fluid flow channel 16 comprises a fluid control feature 24 composed of a plurality of laser-etched lines, such as lines 26, 28, which are devoid of substrate material. In this embodiment, length $l_1$ of each laser-etched line in the plurality is approximately equal in length to length $l_2$ of the fluid flow channel, for a ratio of $l_1$ to $l_2$ of between about 0.9-1.0.

FIG. 1C illustrates an embodiment where a substrate comprises a fluid flow channel 16 defined by opposing substrate-free side channels 30, 32. The opposing side channels are created in the substrate by a laser beam and correspond to regions of substrate where the substrate material is etched or ablated. A fluid control feature 34 is created in the fluid flow path of the flow channel with a laser. In this embodiment, fluid control feature 34 is comprised of a laser-etched line 36 extending essentially from the sample receiving zone 12 to a destination zone 14. Midway along the length of the laser-etched fluid control line 36 is a laser-etched geometric shape 40, in this case a diamond shape, positioned for interaction with a necking region 42 in the opposing side walls.

FIGS. 1D-1L illustrate other embodiments of substrates with fluid control features created by laser ablation of the substrate material. In some embodiments, the fluid control feature is two opposing curved lines that create a constriction in the fluid flow path, as see in FIGS. 1D-1E. In other embodiments, the fluid control feature is comprised of a plurality of two opposing curved lines that create a constriction in the fluid flow, as see in FIG. 1F. In other embodiments, the fluid control feature is comprised of at least two opposing curved lines that create a constriction in the fluid flow and a plurality of lines in the fluid flow channel (FIG. 1G, 1H) or one or more geometric shapes in the fluid flow channel (FIG. 1I). FIG. 1J shows another embodiment, where the fluid control feature comprises a plurality of lines spanning essentially the width of the fluid flow channel, where each line has a proximal end and a distal end, and a first line connecting the proximal ends is an arched line, and a second line connecting the distal ends is an arched line. This embodiment is further discussed with regard to FIGS. 11A-11B.

FIG. 1K illustrates an embodiment of a substrate 10 with a plurality of laser-etched radial flow channels 44, 46, 48. Each of the laser-etched flow channels is in fluid communication with a single, common, sample receiving zone 12 The laser-etched fluid flow channel are created by ablating substrate material to form opposing side walls that define the channels, with adjacent inner fluid flow channels sharing a side wall. That is, inner fluid flow channel 46 shares an opposing side wall with outer channel 44 and with the innermost channel 48. The side wall corresponds to a region of ablated substrate, and is thus a substrate-free channel. In this sense, the term side 'wall' as used herein encompasses a wall that is in the downward z-direction.

FIG. 1L shows an embodiment of a substrate or device 10 comprising a plurality of fluid flow channels, 12, 14, 16, and 18. The substrate is a single, integral material that, in one embodiment, is a laminate of a nitrocellulose substrate that comprises fluid flow channels 12, 14, 16, and 18, and a hydrophobic support layer 31. A single sample receiving zone 20 serves as a common receptacle for the plurality of fluid flow channels to distribute a portion of a liquid sample deposited therein to each of the fluid flow channels in the plurality. Each fluid flow channel in the plurality is comprised of a fluid flow path on or within the substrate, the fluid flow path defined and bounded by opposing substrate free side channels or walls, such as the substrate-free side channels 22, 24. The substrate-free side channels are regions that are substantially devoid of substrate and correspond to a gap or open region where the hydrophobic support layer 31 is exposed. Each fluid flow channel comprises a label zone, a capture zone, and a fluid flow control feature. In the embodiment of FIG. 1L, the fluid control feature is disposed between the label zone and the capture zone in each fluid flow channel. For example, fluid flow channel 18 is comprised of a label zone 26, a fluid flow control feature 28 and a capture zone 30. The fluid flow control feature is a substrate-free region having a geometric shape that controls rate of fluid flow and/or uniformity of flow of a leading edge of a moving fluid, as will be described below. Fluid flow control feature 28 is dimensioned to narrow the fluid flow path in a fluid flow channel with a non-angular shape. That is, the fluid control feature is dimensioned to restrict fluid flow in the fluid flow channel with essentially non-angular dimensions.

A skilled artisan will appreciate that the embodiments shown in FIGS. 1A-1L, and elsewhere infra, can be created by a means other than laser-etching, such as a chemical or mechanical means.

Figure 2A:
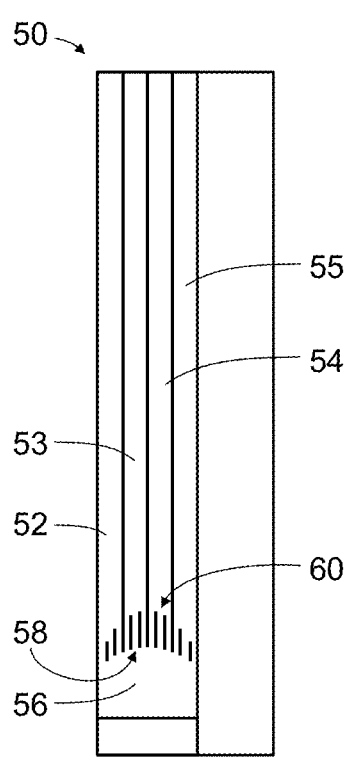
FIGS. 2A-2C illustrate substrates with a plurality of fluid flow channels comprising a fluid control feature for multiplex analysis of a fluid sample.
Figure 2B:
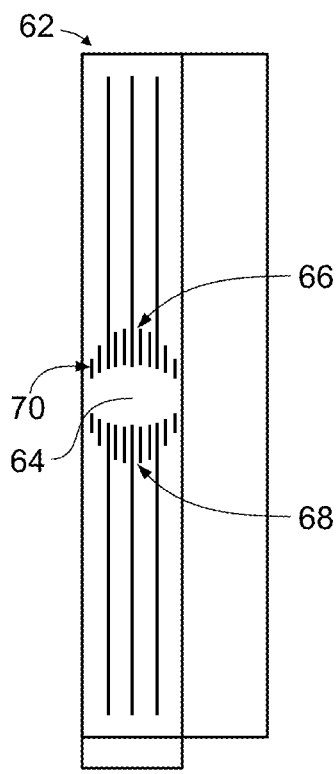
Figure 2C:
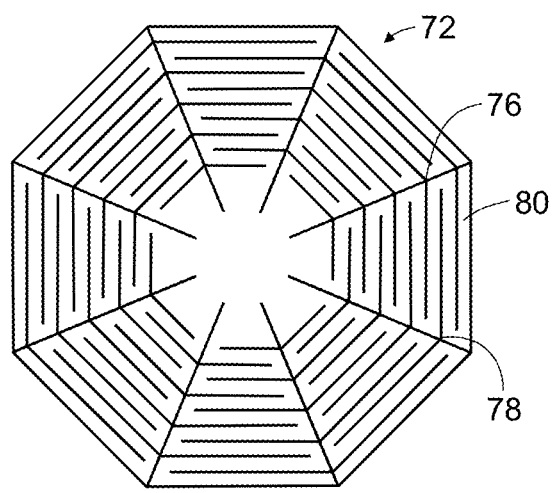
Figure 7:
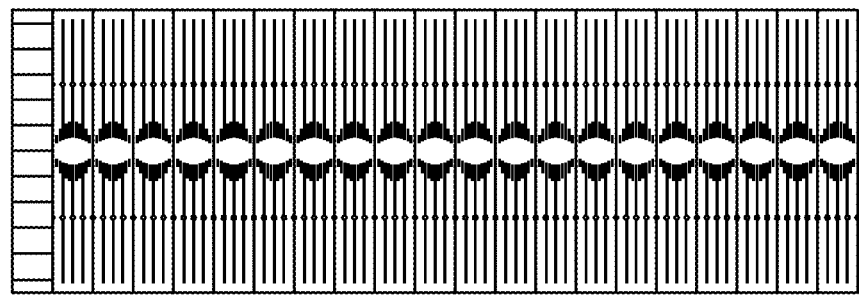
Figure 8:
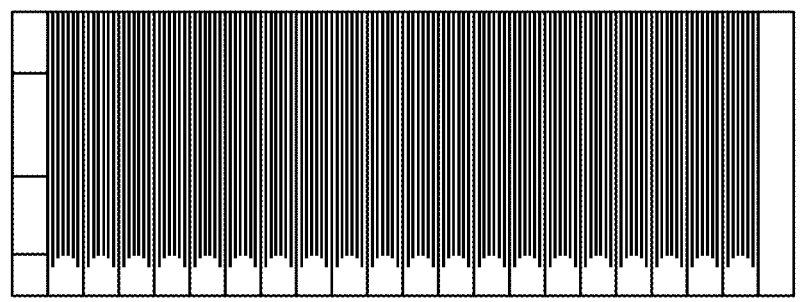
Figure 9:
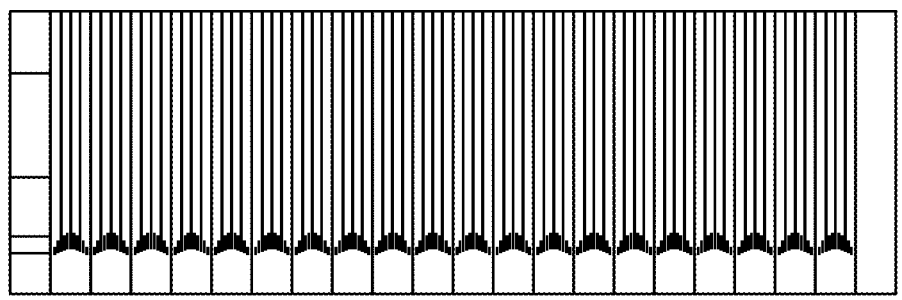

FIGS. 2A-2C illustrate other embodiments of devices or substrates with a plurality of fluid flow channels comprising a fluid control feature, for multiplex analysis of a fluid sample. In FIG. 2A, a single substrate 50 is etched with a laser to remove portions of the substrate to form a plurality of fluid flow channels, in this embodiment, the plurality is composed of four fluid flow channels 52, 53, 54, 55. Each fluid flow channel has opposing substrate-free side walls or channels that define and bound a linear fluid flow path, with adjacent channels sharing a substrate-free side wall. Each fluid flow channel is in fluid communication with a single, common sample receiving zone 56. Each channel has a fluid control feature, such as fluid control feature 58 in channel 53, where the fluid control feature is composed of two parallel, offset lines where substrate is etched or removed. In one embodiment, the parallel, offset lines are of approximately equal length. The plurality of fluid control features (as represented by 58) collectively define a master control feature 60 configured to control the rate of fluid flow from the common sample receiving zone into each fluid flow channel on the substrate and/or the uniformity of fluid flow in each fluid flow channel. The master control feature 60 is comprised of the collection of individual channel fluid control features, where each individual channel's fluid control feature is comprised of at least two parallel, offset laser-etched substrate-free lines, each line having a proximal end and a distal end. A master imaginary line connecting the proximal ends is an arched imaginary line, and a second master imaginary line connecting the distal ends is an arched imaginary line.

FIG. 2B illustrates a single substrate 62 for multiplex analysis of a fluid sample. A single, common sample receiving zone 64 is in fluid communication with a plurality of fluid flow channels, where the plurality in this embodiment is eight, and wherein a portion of the plurality of fluid flow channels has a fluid flow direction opposite that of the remaining portion of the plurality of fluid flow channels. Each fluid flow channel in the substrate is created by laser etching substrate material to remove the substrate and form substrate-free channel sidewalls essentially void of substrate material, for fluid flow in each channel where substrate material remains intact. At the junction between the sample receiving zone and the entry to each individual fluid flow channel is a fluid control feature, such as fluid control features 66, 68, which are representative. Each fluid control feature is composed of two (or more) parallel, offset lines created by removing substrate. In one embodiment, the parallel, offset lines are of approximately equal length, although lines of unequal length are contemplated. The plurality of individual channel fluid control features on one side of the sample receiving (as represented by 66) collectively define a master control feature 70 configured to control the rate of fluid flow from the common sample receiving zone into each channel on the substrate and/or the uniformity of fluid flow in each fluid flow channel. The master control feature 70 is comprised of the collection of individual channel fluid control features, where each individual channel's fluid control feature is comprised of at least two parallel, offset laser-etched substrate-free lines, each line having a proximal end and a distal end. An imaginary master line connecting the proximal ends is an arched imaginary line, and a second imaginary master line connecting the distal ends is an arched imaginary line.

FIG. 2C illustrates a substrate 72 having an etched pattern of fluid flow channels for multiplex analysis of a sample placed in a common, single sample receiving zone 74. The single, integral substrate 72 is exposed to a laser beam to create a plurality of fluid flow paths emanating from the common sample receiving zone. Etched side walls define each flow channel, such as substrate-free side walls 76, 78 that define channel 80. Fluid control features in channel 80 are comprised of a series of laser-etched lines where substrate is removed, the lines configures to guide fluid entering the channel in an undulating or s-pattern.

FIGS. 3-9 show substrates with laser-etched fluid flow patterns, including fluid control features, according to other embodiments.

Studies were performed to demonstrate fluid control features configured to control rate of a fluid flow in the first fluid flow channel and/or control uniformity of rate of flow of a leading edge of a moving fluid in the first fluid flow channel. In a first study, a substrate with a plurality of fluid flow channels having opposing side walls, each side wall created by laser ablation of the substrate material, was prepared. Each fluid flow channel comprised a fluid control feature composed of a series of parallel, evenly spaced and evenly sized laser-etched lines. The fluid control feature was disposed at a junction between the sample receiving zone and the fluid flow channel. A fluid with a blue dye was placed in the sample receiving zone and the rate of fluid flow in the flow channel and the shape of the leading edge of the moving fluid front in each channel was assessed. A short time after deposition of the blue fluid, a photograph of the substrate with the plurality of fluid flow channels was taken, and a rendering of the photograph is shown in FIG. 10A.

Test substrate 82 has three fluid flow channels, 84, 86, 88, each with a fluid control feature, such as feature 90 in channel 84. The leading edge of the moving fluid front is indicated at 92 in channel 84. As seen, the leading edge of the moving fluid front in each channel is at approximately the same position, indicating the rate of fluid flow in each channel on the substrate is essentially the same. In one embodiment, the rate of fluid flow in each channel on the substrate is within about 10%, 8%, 7%, 6%, 5%, 4%, 3%, 2% or 1% of the rate of fluid flow of all other channels on the substrate. In one embodiment, the rate of fluid flow in each channel on the substrate is within about 10%, 8%, 7%, 6%, 5%, 4%, 3%, 2% or 1% of the rate of fluid flow of more than 75%, 80%, or 90% of other channels on the substrate.

Also, the result in FIG. 10A shows that the leading edge 92 of the moving fluid front has a uniform presentation as it travels down the fluid flow channel. With reference to FIGS. 11A-11C, presentation of the leading edge of the moving fluid front in a fluid flow channel is illustrated. In FIG. 11A, the leading edge 94 has an essentially flat or essentially uniform leading edge across the width of the channel. Examples of a non-uniform leading edge of moving fluid flow are shown in FIGS. 11B-11C, where the leading edge is concave (FIG. 11B) or convex (FIG. 11C) in its presentation. It will be appreciated that a uniform or flat leading edge may have a minor amount of concavity or convexity, particularly at the edge of the flow channel with a side wall of the channel. However, so long as the leading edge of the fluid front when viewed macroscopically is essentially flat across the width of the fluid flow channel, the leading edge is referred to herein as essentially flat. In one embodiment, the leading edge of the moving fluid front has a radius of curvature that is equal to or greater than the width of the fluid flow channel. In another embodiment, the leading edge of the moving fluid front has essentially no visually observable curvature. In one embodiment, the moving or advancing fluid front is a single advancing fluid front spanning the width of the fluid flow channel (i.e., the advancing fluid front extends the width defined by opposing channel side walls), the fluid flow channel extending from the exit of the sample receiving zone to a destination zone.

FIG. 10B illustrates a fluid flow channel without a fluid control feature, where the leading edge 96 of the moving fluid front has a convex curvature. This fluid flow channel serves as a comparator and control to the fluid flow channels of FIG. 10A where the fluid control feature was configured to provide a uniform or essentially flat leading edge of the moving fluid front.

In another study, a substrate was exposed to a laser beam to create a plurality of fluid flow channels, as depicted in FIGS. 12A-12B. In this study, a substrate of nitrocellulose was exposed to a $CO_2$ laser to create side walls to define a plurality of fluid flow channels. Each fluid flow channel was exposed to the $CO_2$ laser beam to create by ablation of the nitrocellulose a fluid control feature. As seen in FIGS. 12A-12B, the fluid control feature in each channel was comprised of a series of etched, parallel and offset lines, where an imaginary line drawn to connect the distal end of each line is arched. The fluid control element in the fluid flow channels on the substrate of FIG. 12A are composed of n lines, where n is greater than 3. The fluid control element in the fluid flow channels on the substrate of FIG. 12B are comprised of 3 lines. The fluid control elements are disposed at a junction between the sample receiving zone of each channel and the fluid control element in each channel. A fluid with a blue dye was placed in each sample receiving zone, starting with the channel on the left side of the substrate. The rate of fluid flow in the flow channel and the shape of the leading edge of the moving fluid front in each channel were assessed. A short time after deposition of the blue fluid, a photograph of the substrate with the plurality of fluid flow channels was taken, and a rendering of the photograph is shown in FIGS. 12A-12B. The leading edge of the moving fluid front in each channel is slightly offset from the adjacent channel due to the time lapse in applying the fluid sample to each sample receiving zone. Once this time lapse is accounted for, it is seen that the rate of fluid flow in each channel on the substrate is essentially the same. In comparing the rate of fluid flow in the channels of the substrate of FIG. 12A to that of the channels in the substrate of FIG. 12B, it is seen that the rate of fluid flow in the channels of substrate in FIG. 12B is faster. That is, the fluid control element when comprised of a series of 3 parallel, offset substrate-free lines with a large line pitch results in a fluid flow rate faster than provided by a fluid control element composed of a series of n>3 lines with a small line pitch. From this study, it can be appreciated how the shape and/or design of the fluid control element can be configured to control rate of fluid flow in a fluid flow channel.

The study depicted in FIGS. 12A-12B also illustrates that the fluid flow element comprised of a series of parallel, offset laser etched lines achieved a uniform or flat leading edge of moving fluid front. Presentation of the leading edge of the moving fluid front in a fluid flow channel to be essentially flat or essentially uniform is advantageous and desired, as discussed infra.

In another study, a nitrocellulose substrate was exposed to a laser to remove or etch away portions of the substrate to create a plurality of fluid flow channels. Each channel comprised a fluid control feature, also created by removing or etching away substrate material, positioned at the junction between a sample receiving zone and an entry to the fluid flow channel. Stated alternatively, a fluid control feature was positioned immediately downstream of the sample receiving zone so that fluid encounters the fluid control feature before traveling down the fluid flow channel. The fluid control feature in the channels depicted in FIG. 13A were each composed of a series of parallel lines, evenly spaced with no offset. The fluid control feature in the channels depicted in FIG. 13B were composed of a series of parallel lines, evenly spaced with an offset where the middle line had a distal end downstream from the distal end of adjacent lines. The fluid control feature in the channels depicted in FIG. 13C were composed of a series of parallel lines, evenly spaced with an offset where the middle line had a proximal end upstream from the proximal end of adjacent lines. A fluid with a blue dye was placed in each sample receiving zone, starting with the channel on the left side of the substrate. The rate of fluid flow in the flow channel and the shape of the leading edge of the moving fluid front in each channel were assessed. In each of FIGS. 13B-13C, a fluid flow channel on the substrate lacking a fluid control feature was included as a control, as seen in the left hand channel of the substrate of these drawings. A short time after deposition of the blue fluid, a photograph of the substrate with the plurality of fluid flow channels was taken, and a rendering of the photograph is shown in FIGS. 13A-13C. The leading edge of the moving fluid front in each channel is slightly offset from the adjacent channel due to the time lapse in applying the fluid sample to each sample receiving zone. Once this time lapse is accounted for, it is seen that the rate of fluid flow in each channel on the substrate is essentially the same.

In one embodiment, the rate of fluid flow in each discrete channel of the plurality of fluid flow channels in the substrate is within about 25%, or 20% or 15% or 10% or 5% of the rate of fluid flow of any other channel in the plurality. Rate of fluid flow is measured as the time for a moving fluid front to move from the sample receiving zone from which the channels in the plurality emanate to a destination zone, for example to the label zone, the capture zone or the terminus of the channel. The rate of fluid flow can be adjusted by altering the dimensions (primarily width and thickness) of each channel, placement of the label zone, the capture zone, or material within a channel. It is desired, in most embodiments, for the moving fluid front (e.g., portion of sample in each channel) to advance along the fluid flow path at about the same rate as adjacent channels so that a test result visible in the capture zone appears at approximately the same time for each use.

The study depicted in FIG. 13A also illustrates that the fluid flow element comprised of a series of parallel laser etched lines with no offset achieved a uniform or flat leading edge of moving fluid front. Presentation of the leading edge of the moving fluid front in a fluid flow channel to be essentially flat or essentially uniform is advantageous and desired, as discussed infra. From this study, it can be appreciated how the shape and/or design of the fluid control element can be configured to control rate of fluid flow in a fluid flow channel. In one embodiment, the fluid control feature is composed of a series of laser-etched parallel lines, having a distal end and a proximal end, where an imaginary line connecting the distal ends of each laser-etched line is a straight line and/or where an imaginary line connecting the proximal ends of each laser-etched line is a straight line.

Based on the foregoing, it can be appreciated that contemplated is a device comprised of a substrate and a support layer. The substrate has a thickness l. Defined on the substrate is a first fluid flow channel having opposing side walls created by exposure of the substrate to a laser. The opposing side walls correspond to laser-treated areas that ablate the substrate material, and render the ablated region impermeable to fluid flow. In one embodiment, the side wall has a thickness l, created by laser ablation of the entire thickness l of the substrate. Thus, absent the support layer of the device, the substrate after laser etching to create the side walls would have a slit or through-hole. A first fluid control feature is defined on the substrate by exposure to a laser, the first fluid control feature controlling (i) rate of a fluid flow in the first fluid flow channel and/or (ii) uniformity of rate of flow of a leading edge of a moving fluid in the first fluid flow channel.

In another aspect, an immunoassay test strip is comprised of a substrate as described herein. The substrate has a fluid flow channel, optionally created by etching away substrate material to form opposing side channels or walls. In the fluid flow channel is a fluid control feature, as described herein, to control (i) rate of a fluid flow in the fluid flow channel and/or (ii) uniformity of rate of flow of a leading edge of a moving fluid in the fluid flow channel. The fluid control feature is a substrate-free feature with a geometric shape. The fluid flow channel also comprises a sample receiving zone, which in a preferred embodiment is a shared sample receiving zone, a label zone and a test zone. The label zone and test zone can each be a destination zone.

With reference to FIGS. 14A-14B, exemplary test strips are shown. Test strip 100 comprises a single, discrete substrate 102 with a single fluid flow channel 104. Fluid flow channel extends from a sample receiving zone 106 to a test zone 108. Located downstream of the sample receiving zone is a fluid control feature 110. In this embodiment, fluid control feature 110 is comprised of opposing, mirror image laser-etched substrate-free lines that together define a constriction region 112 in the fluid flow channel. Downstream of the fluid control feature is a label zone 114. Test zone 108 comprises, in this embodiment, a first test line 116, a second test line 118, and a reference or control line 120.

FIG. 14B is another embodiment of an immunoassay test strip 124 for multiplex analysis of a sample placed on the test strip. Test strip 124 has a single sample receiving zone 126 that is in fluid communication with a plurality of isolated, discrete fluid flow channels. In this particular embodiment, the test strip comprise 8 fluid flow channels emanating from the single sample receiving zone, where a first portion of the fluid flow channels flow in a first direction and a section portion of the fluid flow channels flow in a second, opposing direction. In this embodiment the first portion is equal in number to the second portion, although the two portions can be unequal. Each channel is created by exposing the substrate to a laser beam to etch or ablate the substrate material to create a series of parallel substrate-free side channels or side walls, such as side walls 128, 130. The side walls are impermeable to fluid flow, so that each fluid flow channel is isolated from the next and no cross-fluid communication occurs as a sample travels down a fluid flow channel. Each individual fluid flow channel comprises a laser-etched fluid control feature 132, a label zone 134, and test and control zones, 136, 138.

The substrate and the test strip comprising a substrate are, in one embodiment, comprised of a single, integral piece of material that forms the substrate on which the fluid control element is created and on which the fluid flow channel is disposed. The substrate may have a support layer secured to one side, the support layer generally comprises a hydrophobic and/or impermeable material—such as polyethylene terephthalate, polyesters, silicone, etc. In some embodiments, the test strip is comprised solely and only of the substrate and/or a support layer. In other embodiments, the test strip additionally comprises a second material that is in fluid communication with the substrate. For example, a test strip may comprise a nitrocellulose substrate with laser-etched walls to form a substrate-free channel that is overlaid on another material such as an impermeable backing extending the length of the substrate, and/or the substrate may be abutted with or overlapped with an absorbent material at one end of the channel. Alternatively or in addition, a test strip may include a region comprising one or more materials followed by a region comprising one or more different materials. In this case, the regions are in fluid communication and may or may not partially overlap one another.

The fluid control feature and/or the side walls of a fluid flow channel are created on the substrate using, in one embodiment, a laser. In one particular embodiment, a laser is used to ablate substrate material in a controlled fashion. Laser ablation generally refers to a process for removing a material using incident light of a certain wavelength. In polymeric materials, for instance, the incident light generally induces photochemical changes in the polymer that results in chemical dissolution. Any known laser may be employed in the present invention, including, for instance, $CO_2$ lasers, pulsed light lasers, diode lasers, ND:Yag 1064 nm and 532 nm lasers, alexandrite and Q-switched lasers, pulsed dye lasers, optical and RF lasers, erbium lasers, ruby lasers, and holmium lasers. In a preferred embodiment, a $CO_2$ laser is used to etch a nitrocellulose membrane that is mounted on a supporting fixture. Through use of a moving beam or an x-y table, precision channels are created on the nitrocellulose to define, for example, the fluid control feature. In addition, various other known optical devices may be employed in conjunction with the laser to enhance the channel formation, such as optical lenses, mirrors, etc. In another preferred embodiment, a Nd:YVO4 solid-state laser having picosecond pulses is used, for example at a 532 nanometer wavelength and a 12 picosecond pulse length, a 10 microjoule pulse energy and a 10 kilohertz pulse frequency, with a beam focused on the substrate using a 100 millimeter F-theta lens and a fee rate of 25 milliseconds per second. The parameters for laser ablation of the substrate, such as wavelength, pulse duration, pulse repetition rate, and beam quality, for any given laser can be determined by a skilled artisan.

In one embodiment, the substrate is laser treated to create a plurality of fluid flow channels, where each fluid flow channel in the plurality is physically separated (i.e., by a gap corresponding to a region of ablated substrate) from an adjacent fluid flow channel by a distance of at least about 0.01 mm, 0.025 mm, 0.03 mm, 0.05 mm, 0.07 mm, 0.08 mm, 0.09, 0.1 mm, 0.2 mm. 0.3 mm, 0.4 mm, 0.5 mm, 0.6 mm, 0.7 mm, 0.8 mm, 0.9 mm, or 1 mm, or is between about any two of these discrete values. In one embodiment, the width of each fluid flow channel in the plurality of fluid flow channels is at least about 0.1 mm, 0.2 mm. 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, or 2 mm, or is between about any two of these discrete values.

As discussed above, the test strip comprises, in one embodiment, a label zone and one or more test (or capture or control) zones. In one embodiment, the label zone comprises a mobilizable, detectable species and/or the capture zone comprises an immobilizable species. Examples of detectable species, mobilizable and immobilizable, are known in the art and depend on the analyte of interest (e.g., an infectious agent). Some examples are described infra. With respect to the test strip described herein, the mobilizable, detectable species deposited in the label zone and/or the immobilizable species deposited in the capture zone(s) or control zones are deposited in the form of drops that form an array, as will now be described and discussed with respect to FIGS. 15A-15C and FIGS. 16A-16B. The capture zone, control zone, label zone will be referred to generically as a destination zone.

In each of these exemplary drawings, the destination zone is comprised of an array of drops, where each drop corresponds to a formulation useful for detection of an analyte of interest. That is, the formulation may comprise a mobilizable, detectable species or it may comprise a binding partner or species immobilized to the substrate or it may comprise a species useful as a control. The array, in one embodiment, comprises m drops in one direction and n drops in a second direction, to form an m/n array, where m and/or n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In one embodiment, n and m are the same, and in another embodiment, n and m are of a different value. The arrays depicted in FIGS. 15A-15C are each a 12/15 array, where each drop in the array was deposited onto the substrate from a precision liquid dispensing instrument (Scienion AG). Studies were conducted to evaluate instrument variables on positional accuracy of each dot in the array. In the array of FIG. 15A, each drop was formed by a single droplet of formulation dispensed from the dispensing instrument. In the array of FIG. 15B, each drop of the array was formed by dispensing 5 droplets of formulation. In the array of FIG. 15C, each drop in the array was formed by dispensing 10 droplets of formulation. The dispensing instrument permits a user to select droplet volume, drop pitch, and other variables. A user can also select whether multiple droplets are deposited at each position in the array in a single pass of the instrument dispensing head or in multiple passes of the instrument dispensing head. In FIG. 16A, the 10/10 array was created by dispensing 20 droplets (380 pL each) at each m/n position in the array, where 10 droplets were deposited in a first pass to each m/n position by the dispensing head and 10 droplets were deposited in a second pass by the dispensing head to each m/n position in the array. In FIG. 16B, the 10/10 array was created by dispensing 20 droplets (380 pL each) at each m/n position in the array with a single pass of the dispensing head to each m/n position in the array. That is, the dispensing head deposited 20 droplets of formulation at each m/n position in the array before moving on to the next m/n position in the array. In comparing the positional accuracy of each drop in the 10/10 array of FIGS. 16A-16B, it is seen that fewer drops with multiple passes of the dispensing head improves positional accuracy of the drops in the array. That is, the array of FIG. 16A, created by depositing 10 drops at each m/n position in the array per pass of the dispensing head at each m/n position has a more uniform pitch between drops of the array and better positional accuracy. Other test strips were constructed to have a capture zone comprised of a 30/6 (m/n) array of drops comprising goat anti-mouse IgG antibody, each drop in the array having a pitch of 100 μm and a volume of 350 picoliters (pL). In another study, a 6/6 (m/n) array of drops comprising mouse anti-flu fluorescent beads, each drop in the array having a pitch of 100 μm and a volume of 350 pL was deposited to form a label zone.

Accordingly, in one embodiment, a destination zone on a test strip is comprised of an m/n (or m×n) array of discrete drops or dots, where m is greater than or equal to one (1) and n is greater than or equal to zero (0), wherein when n is greater than zero each dot in the m×n array is separated from an adjacent dot by a distance x. In another embodiment, m is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and n is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and each dot in the m×n array is separated from an adjacent dot by a distance x. In another embodiment, n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and n is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and each dot in the m×n array is separated from an adjacent dot by a distance x. In one embodiment, x is also referred to as a pitch or spacing, and is between about 20-1000 μm, or between about 50-500 μm, or between about 75-500 μm, or between about 100-500 μm, or between about 150-500 μm, or between about 150-300 μm, or between about 150-250 μm, or between about 200-500 μm.

In another embodiment, the volume of formulation deposited on the substrate to form each drop (or dot) in the array is between about 20-1000 pL, or between about 50-800 pL, or between about 75-800 pL, or between about 100-600 pL, or between about 150-550 pL, or between about 200-500 pL, or between about 200-450 pL.

Figure 17:
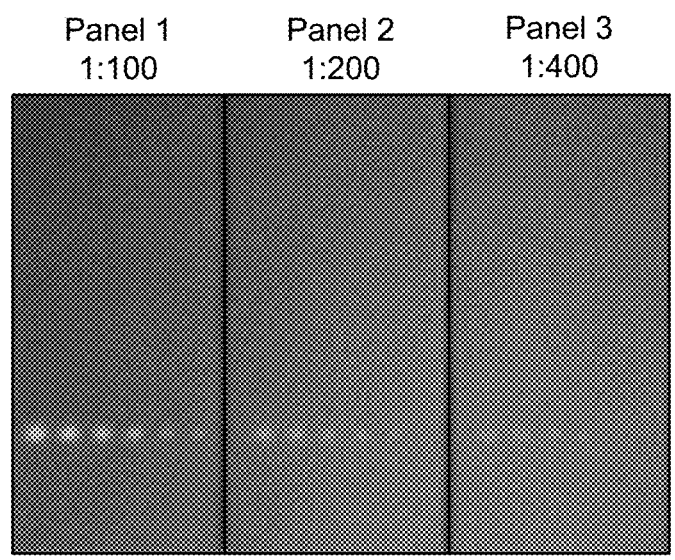
FIG. 17 is a photograph of a substrate with three fluid flow channels, each with a capture zone of a 6/1 drop array, with the number of droplets deposited at each position in the array varying from 80 droplets to 5 droplets and with varying concentration of reagent (Panel 1, 1:100; Panel 2, 1:200; Panel 3, 1:400)

The test strips illustrated in FIG. 17 show studies conducted to evaluate these parameters in creating capture zone comprised of an array of drops. FIG. 17 is an artist's rendering of a photograph of three test strips, designated as Panel 1, Panel 2 and Panel 3. On each test strip was deposited a capture zone of a 6/1 drop array, where each drop in the array has a different number of droplets deposited. With respect to Panel 1, a formulation with an antibody concentration of 1:100 was prepared and used to create the 6/1 array. The drop in position 1/1 of the array (the m position 1 being at the left most side of the array) has 80 droplets, each droplet having a volume of 400 pL. The drop in position 2/1 of the array has 60 droplets, each droplet having a volume of 400 pL. The drop in position 3/1 of the array has 40 droplets, each droplet having a volume of 400 pL. The drop in position 4/1 of the array has 20 droplets, each droplet having a volume of 400 pL. The drop in position 5/1 of the array has 10 droplets, each droplet having a volume of 400 pL. The drop in position 6/1 of the array has 5 droplets, each droplet having a volume of 400 pL. The diminishing visibility of each drop in the array is apparent. Panel 2 shows a similar test strip, where the formulation dispensed to form the array was at a 1:200 antibody concentration. Panel 3 shows a similar test strip, where the formulation dispensed to form the array was at a 1:400 antibody concentration. Thus, a skilled artisan can appreciate that the array created can vary the concentration of component in the formulation to be dispensed, droplet volume, droplet number, and other factors.

Figure 18:
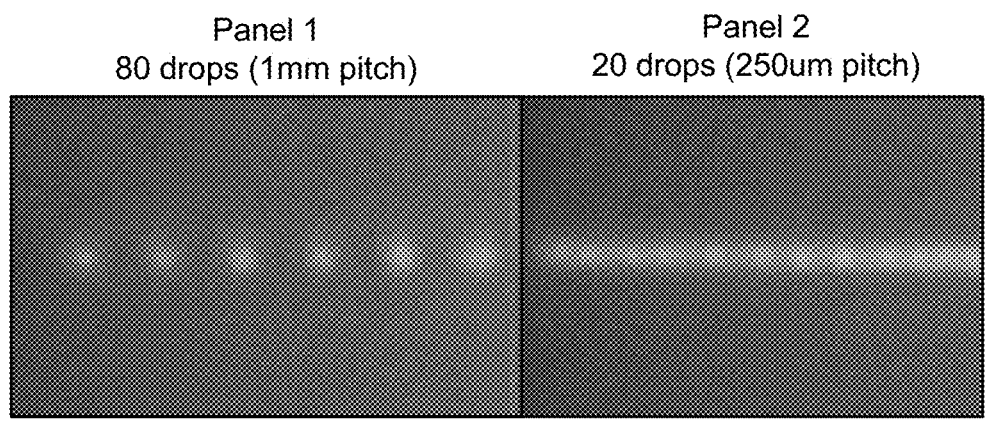
FIG. 18 is a photograph two test strips, each with a capture zone of a 6/1 drop array, where the capture zone on the strip shown on the left has 80 droplets deposited in each position on the 6/1 array, with a 1 mm pitch between drops, and the capture zone on the strip in the right panel has 20 droplets deposited in each position on the 6/1 array, with a 250 µm dot pitch.

FIG. 18 is an artist's rendering of a photograph two test strips (Panel 1 and Panel 2). Each test strip has a capture zone of a 6/1 drop array, where the capture zone on the strip shown on the left (Panel 1) has 80 droplets deposited in each position on the 6/1 array, with a 1 mm pitch between drops. After use, the drops of the array remain distinct, separated from an adjacent drop. In contrast, the capture zone on the strip in the right panel (Panel 2) has 20 droplets deposited in each position on the 6/1 array, with a 250 μm dot pitch. After use, the drops of the array blend together, with no pitch or spacing between adjacent drops.

Figure 19A:
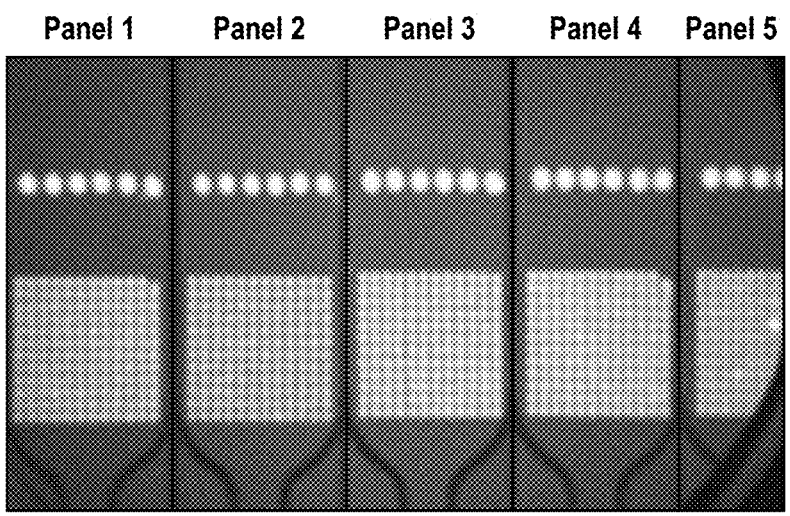
FIG. 19A is a photograph of a substrate with five fluid flow channels, each with fluid control feature, a label zone formed of a 12/12 drop array and a test (capture) zone composed of a 6/1 drop array.

Studies were conducted to evaluate the rate of flow and uniformity of the leading edge of a moving fluid front on substrates with a laser-etched fluid control feature and a label zone of a drop array. In these studies, a nitrocellulose substrate was exposed to a $CO_2$ laser beam to create a plurality of fluid flow channels, each with a fluid control feature. A 12/12 drop array was deposited downstream of the fluid control feature in each channel, the drop array comprised of reagent with an anti-flu A nucleoprotein antibody attached to a europium bead (a mobilizable, detectable species). A test zone was created in each channel, the test zone comprised of a 6/1 drop array, each drop comprised of a reagent to deposit an immobilizable an anti-flu A nucleoprotein antibody. FIG. 19A is a photograph of a substrate with five fluid flow channels created thereon by laser etching. Each fluid flow channel has a fluid control feature, a label zone formed of a 12/12 drop array and a test (capture) zone composed of a 6/1 drop array.

Figure 19B:
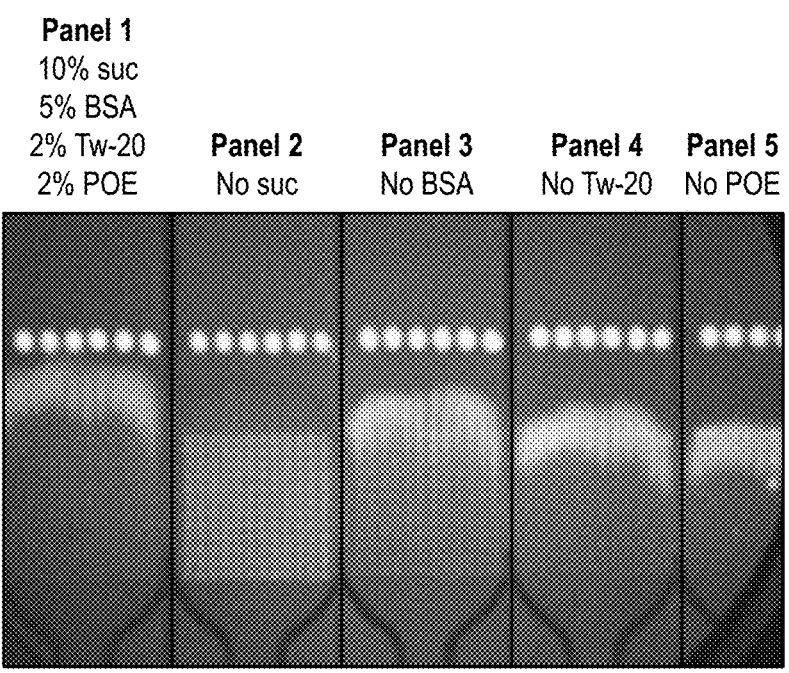
FIGS. 19B-19C are photographs of the substrate and five fluid flow channels of FIG. 19A, where release of mobilizable, detectable anti-flu A nucleoprotein antibody is evaluated using release agents with different formulations.
Figure 19C:
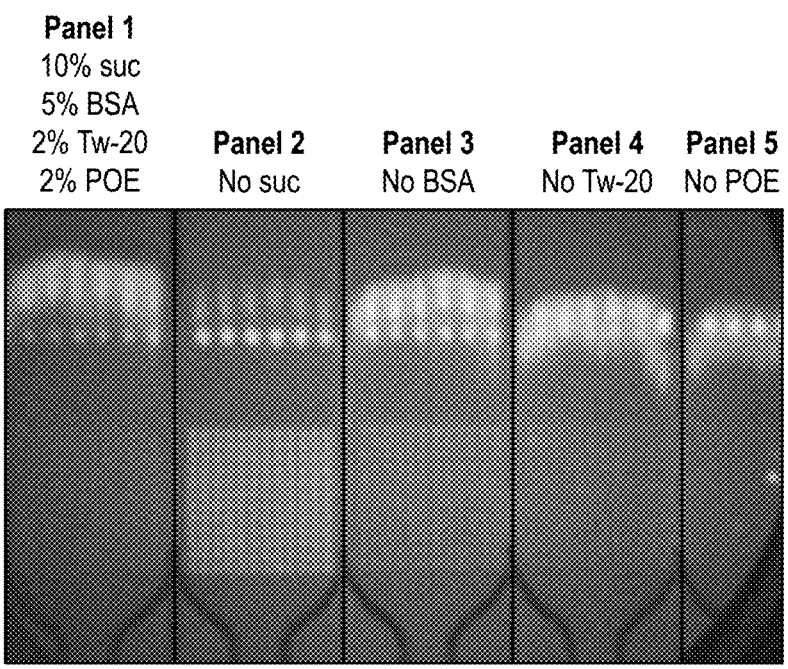

A release reagent composed of a borate buffer with 10% sucrose, 5% bovine serum albumin (BSA), 2% polyoxyethylene (BRIJ), and 2% polyoxyethylene sorbitan monolaurate (TWEEN® 20) was prepared. Similar release reagents were prepared that omitted one of the components—no sucrose (Panel 2), no BSA (Panel 3), no TWEEN® (Panel 4) or no BRIJ® (POE) (Panel 5). Each reagent was placed on a fluid flow channel, and a photograph was taken after the moving fluid front crossed the distal or downstream edge of the capture zone (FIG. 19B) and again when the moving fluid front crossed the test zone (FIG. 19C). The influenced of the release reagent on release of the mobilizable species in the array of the capture zone is apparent, where sucrose or a sugar is beneficial to effect release (e.g., compare FIG. 19B Panel 2 to Panels 1, 3, 4 and 5). The study also suggests that both surfactants are not needed.

Figure 20A:
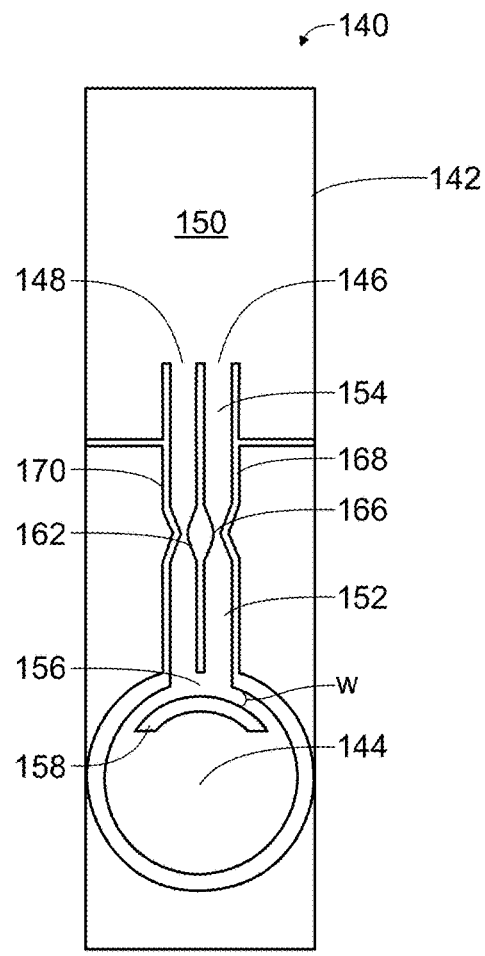
FIG. 20A is an illustration of a test strip with two fluid control features.

Another embodiment of a substrate is shown in FIG. 20A. Test strip 140 comprises a single substrate 142 with a single, common sample port 144 for delivery of sample to two adjacent, parallel fluid flow channels 146, 148. The two channels terminate into a common absorbent zone 150. Substrate 142 is a single, discrete, continuous and/or uninterrupted layer from the sample port to the absorbent zone on which the laser-etched features are created. Each channel 146, 148 comprises a conjugate zone, such as conjugate zone 152 in channel 146, and a capture zone, such as conjugate zone 154 in channel 146, each zone having an array of discrete dots composed of a reagent with a binding member, as will be discussed with respect to FIG. 20C infra. At an ingress point 156 to the fluid flow channels, the ingress point disposed at an edge of the sample zone and a distal end of a fluid flow channel, is a fluid control feature 158. In one embodiment, the array is an m/n (or m×n) array of discrete drops or dots, where m is greater than or equal to one (1) and n is greater than or equal to zero (0).

Test strip 140 comprises two fluid control features. The first fluid control feature 158 is created via exposure of substrate 142 to a laser and is dimensioned to meter, control, and/or guide a fluid sample deposited in the sample receiving zone. Fluid control feature 158 is positioned a distance w from the laser-etched inner side wall 160 that defines the sample receiving zone. Fluid control feature 158 in this embodiment is an arc with an arc length l. As can be appreciated, arc length l can be varied to meter, control, and/or guide a fluid sample deposited in the sample receiving zone into the fluid flow channels, whereas arc length l increases the rate of fluid flow into the fluid flow channels decreases.

The second fluid control feature on test strip 140 is positioned in the fluid flow channel and in this embodiment is a diamond shaped control feature 162. The diamond-shaped fluid control feature defines a pinch point 166 in each adjacent fluid flow channel that influences the rate of fluid flow in the channel. In this embodiment, a laser-etched side wall of each fluid flow channel, such as side walls 168, 170, are configured to enhance or further narrow the pinch point. It will be appreciated that the width of the channel at the pinch point can be varied by altering the dimensions of the fluid control feature and the configuration of the side walls adjacent the fluid control feature. In one embodiment, the side walls adjacent the fluid control feature are straight and do not contribute to creation of a pinch point, and in another embodiment, the side walls adjacent the fluid control feature are angled or v-shaped to enhance the pinch point relative to that created by the fluid control feature alone.

In one embodiment, a substrate having a fluid control feature positioned in the sample receiving zone and/or near a point of fluid ingress from the sample receiving zone and a distal end of a fluid flow channel is contemplated, where the fluid control feature is configured to be an arc. In one embodiment, the arc has a length l that for a circle comprising the arc has an arc radius (r) that ranges from $1=2\pi r(C/360)$, where C is the central angle of the arc in degrees (°) and ranges from between about 10-180°. In other embodiments, C is between about 10-170°, 15-160°, 20-150°, 30-150°, 40-150°, 50-150°, 60-150°, 70-150°, 80-150°, 90-150°, 100-150°, 20-140°, 30-140°, 40-140°, 50-140°, 60-140°, 70-140°, 80-140°, 90-140°, 100-140°, 20-130°, 30-130°, 40-130°, 50-130°, 60-130°, 70-130°, 80-130°, 90-130°, 100-130°, 20-120°, 30-120°, 40-120°, 50-120°, 60-120°, 70-120°, 80-120°, 90-120°, 100-120°, 20-110°, 30-110°, 40-110°, 50-110°, 60-110°, 70-110°, 80-110°, 90-110°, 100-110°, 20-100°, 30-100°, 40-100°, 50-100°, 60-100°, 70-100°, 80-100°, 90-100°, 100-100°, 20-90°, 30-90°, 40-150°, 50-90°, 60-190°, 70-90°, or 80-90°.

In another embodiment, the fluid control feature is configured to be an arc having an arc length l equal to r*C, where C is the central angle of the arc in radians, and r is the radius of the arc. In this embodiment, the arc length l is equal to the radius of a circle comprising the arc.

In another embodiment, the arc-shaped fluid control feature is a distance w from the laser-etched sidewall that defines the sample receiving zone, where w ranges from about 1 μm-5 mm (0.001 mm-5 mm), 0.01 mm-5 mm, 0.01 mm-3 mm, 0.01 mm-2.5 mm, 0.01 mm-2 mm, 0.1 mm-5 mm, 0.1 mm-3 mm, 0.1 mm-2.5 mm, 0.1 mm-2 mm, 1 mm-5 mm, 1 mm-4 mm, 1 mm-3 mm, 1 mm-2.5 mm, or 1 mm-2 mm.

In another embodiment the width of the substrate-free laser-etched side walls (or side channels) defining the fluid flow channel is different from the width of the substrate-free laser-etched side wall(s) defining the sample receiving zone. In the test strip shown in FIG. 20A, the laser-etched side walls forming the fluid flow channels have a width that is less than that of the laser-etched side walls forming the sample receiving zone. Accordingly, in one embodiment, a test strip is contemplated, where the width of the side wall forming the sample receiving zone is equal to or greater than the width of the side walls forming the fluid flow channel, where ratio of sample receiving zone wall width to fluid flow channel side wall width is between about 1-10, 1-8, 1-7, 1-6, 1-5, 1.1-10, 1.1-8, 1.1-7, 1.1-6, 1.1-5, 1.2-10, 1.2-8, 1.2-7, 1.2-6, 1.2-5, 1.3-10, 1.3-8, 1.3-7, 1.3-6, 1.3-5, 1.4-10, 1.4-8, 1.4-7, 1.4-6, 1.4-5, 1.5-10, 1.5-8, 1.5-7, 1.5-6, or 1.5-5.

In another embodiment, the substrate is a nitrocellulose substrate laminated to or in direct contact with a base layer. In one embodiment, the base layer is a hydrophilic base layer and in another embodiment the base layer is a hydrophobic base layer. Together the nitrocellulose substrate and the base layer form a laminate. With reference to the substrate illustrated in FIG. 20A, the substrate is contemplated for use with a hydrophilic base layer and has certain design features, now to be mentioned. The width of the wall forming the sample receiving zone is wider than the width of the walls forming the fluid flow channels. In this example, the wall forming the circular sample receiving zone is about 2 mm in width and the wall forming the fluid flow channel is about 400 µm, for a ratio of 5. The surface area of exposed substrate in the sample receiving zone is greater than the surface area of the fluid flow channels that emanate from and/or are in fluid communication with the sample receiving zone. In embodiments, the surface area of exposed substrate in the sample receiving zone is 5%, 10%, 15%, 20% or 25% greater than the surface area of the fluid flow channels that emanate from and/or are in fluid communication with the sample receiving zone. The fluid control feature positioned in the fluid flow channel is configured to create a pinch point whilst permitting laminar fluid flow in the channel. This is achieved, in part, by an angle in the side wall of the fluid flow channel that corresponds to the points of the fluid flow features that extends into each fluid flow channel. Also, the substrate material in the laser-created fluid flow feature is substantially completely removed by the laser, thus exposing the base layer to the environment of use in the fluid flow feature.

In another embodiment, the substrate illustrated in FIG. 20A is contemplated for use with a hydrophobic base layer. In this embodiment, the design features may be altered from those that would be present when the base layer is hydrophilic. For example, the width of the wall forming the sample receiving zone may be the same as or small than the width of the walls forming the fluid flow channels. For example, the wall forming the circular sample receiving zone is about 400 µm in width and the wall forming the fluid flow channel is about 400 µm, for a ratio of 1. The surface area of exposed substrate in the sample receiving zone is the same as or less than the surface area of the fluid flow channels that emanate from and/or are in fluid communication with the sample receiving zone. In embodiments, the surface area of exposed substrate in the sample receiving zone is equal to or 5%, 10%, 15%, 20% or 25% less than the surface area of the fluid flow channels that emanate from and/or are in fluid communication with the sample receiving zone.

In one embodiment, the volume of the sample receiving zone is selected to receive a sample volume into the sample receiving zone with no observable fluid flow over a channel barrier, side wall and/or fluid control feature. In another embodiment, the substrate material within the laser-etched boundaries of a fluid control feature is entirely removed by laser ablation, whereas in other embodiments, the substrate material within the laser-etched boundaries of a fluid control feature remains intact or partially intact.

Figure 20B:
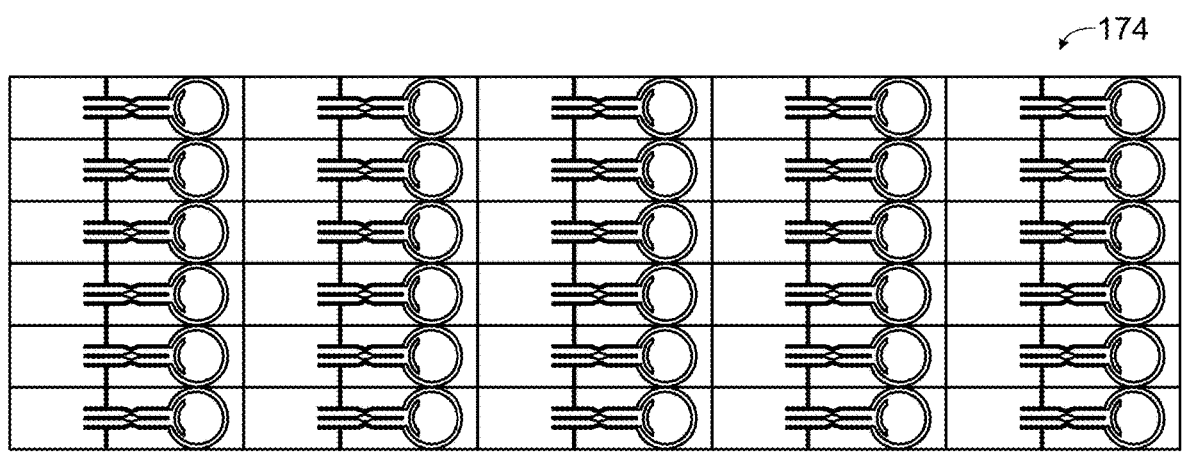
FIG. 20B is an array of test strips.

The test strip depicted in FIG. 20A is shown in array format in FIG. 20B. Array 174 is a 5×6 array for a total of 30 test strips on a single substrate. It will be appreciated that the 5×6 array is merely exemplary, and an array of any size, m×n, is contemplated and can be fabricated, where m and n can be the same or different and are any integer ranging from 1 to 1,000, where when m is 1, n is 0, 1 or 2 or more.

III. Methods of Use

The device described herein is contemplated for use in detection of any pathogenic or infectious agent. In a first aspect, a device for determining presence or absence of an analyte is provided. In one embodiment, the device is constructed for detection of a plurality of analytes. At least one or more of the analytes is associated with disease or infection in a human subject. In some embodiments, the analytes comprise one or more species or subtypes of analytes, each indicative of a disease or infection where discrimination of the species or subtypes aids in staging a disease or infection, in diagnosis, or in determining a treatment or therapeutic plan. The analytes may be the infectious or disease causing agents or may be analytes arising due to the presence of the infectious or disease causing agents, such as antibodies. Various embodiments of the device will be described with reference to certain drawing figures.

In a preferred test strip, each discrete channel in the plurality of fluid flow channels has a fluid flow path in communication with the common zone, where each fluid flow path is discrete—i.e., individually separate and distinct—from the fluid flow path of the other fluid flow channels in the plurality. "Fluid flow path" thus refers to that portion of each channel that begins at a point of its departure from a common zone in the structured material and extends to its terminus or to its termination at a second common zone. Each discrete fluid flow channel in the plurality comprises a label zone and a capture zone. Each label zone comprises a mobilizable, detectable species able to bind to an analyte of interest, which as mentioned above may be an infectious agent or an analyte indicative of the infectious agent, such as an antibody against the infectious agent. Examples are given below.

Capture zone (sometimes referred to herein and in the art as a test line or test zone) is positioned downstream of the label zone in each discrete channel. The capture zone comprises an immobilized species with binding affinity for the mobilizable detectable species in the label zone with which it is associated. Binding affinity intends indirect binding or direct binding between two species, such as direct binding of an antigen to an antibody or indirect binding of a secondary antibody to a conjugate formed of a primary antibody and an antigen, where the secondary antibody and primary antibody have binding affinity. For example, in one embodiment, an antibody in the patient sample is indicative of presence of infection by an infectious agent, and the antibody in the patient sample binds a mobilizable, detectable species comprised of a non-human antibody with binding affinity for the antibody in the patient sample or an antigen of or from the infectious agent indicative of the suspected infection.

The test device comprises a sample receiving zone configured to receive a liquid sample. Typically, the sample is from a subject suspected of having an infection due to an infectious agent, and examples of types of patient samples and of infectious agents are described below. As described above, the sample receiving zone is positioned to distribute the sample to each of the test strips in the device, and thus is in contact with the common zone of each test strip from which each discrete channel in the plurality of fluid flow channels emanates.

Test strip or devices optionally comprise a control line or zone and/or a reference line or zone. If present, such zones or lines comprise an immobilized species with binding affinity for a detectable moiety deposited on or formed in a channel on the device upstream of the control or reference line or zone.

As mentioned above, in one embodiment, the capture zone comprises an immobilized species that directly binds an antibody present in the patient sample, the antibody being one raised by the patient's immune system against the infectious agent of interest and suspected of being the cause of infection in the patient. In another embodiment, the capture zone comprises an immobilized species that binds a conjugate formed on the test device, the conjugate comprised of (i) the mobilizable, detectable species in the first label zone and (ii) an antibody present in the patient sample, the antibody being one raised by the patient's immune system against the infectious agent of interest and suspected of being the cause of infection in the patient.

In one embodiment, a capture zone in a channel within the plurality comprises an immobilized species that directly binds antibody against the infectious agent, the antibody being one raised by the patient's immune system against the infectious agent of interest and suspected of being the cause of infection in the patient. In another embodiment, the capture zone comprises an immobilized species that binds a conjugate formed on the test device, the conjugate comprised of (i) the mobilizable, detectable species in the second label zone and (ii) an antibody present in the patient sample, the antibody being one raised by the patient's immune system against the infectious agent of interest and suspected of being the cause of infection in the patient.

For purposes of illustration, an exemplary test strip for detection of an infectious agent associated with Lyme disease will be described. In this exemplary test strip, it is desired to determine whether a subject is at risk of Lyme disease or has Lyme disease, or, alternatively, it is desired to determine if infection with a *Borrelia* species, such as but not limited to *Borrelia burgdorferi, Borrelia afzelii, Borrelia garinii, Borellia japonica*, is at an early stage or a late stage of infection. To achieve these desires, a test strip that comprises a plurality of discrete fluid flow channels in fluid communication with a common, single, individual sample receiving zone is provided, and a patient's sample is deposited on or in the sample receiving zone. The sample receiving zone may be the common zone (discussed above) to a test strip or may be a separate material in fluid communication with the common zone of one or more test strips. A portion of sample placed in the sample receiving zone is distributed to each channel in the plurality of fluid flow channels. As the sample flows in a downstream to upstream direction beginning at the common zone or sample receiving zone, the sample reaches the label zone associated with that channel, where a mobilizable, detectable species is deposited. The mobilizable, detectable species in the exemplary test strip for staging or detecting infection by a species in the *Borrelia* genus is, in a first embodiment, a non-human, anti-human antibody that has or is associated with a detectable label. The non-human, anti-human antibody is, in some embodiments, a non-human, anti-human IgG antibody bearing a detectable label, such as a fluorescent, chemiluminescent, or other optically detectable tag, such as a bead or chemical moiety. The non-human, anti-human antibody is, in some embodiments, a non-human, anti-human IgM antibody bearing a detectable label, such as a fluorescent, chemiluminescent, or other optically detectable tag, such as a bead or chemical moiety. In this exemplary test strip, the detectable non-human, anti-human IgM antibody is deposited in the label zone of one of the discrete channels in the plurality of fluid flow channels. In the label zone of another discrete channel in the plurality of fluid flow channels is a detectable non-human, anti-human IgG antibody. Specific examples include a detectable goat anti-human IgM antibody in one label zone in a first discrete fluid flow channel and a detectable goat anti-human IgG antibody is deposited in a label zone of another discrete fluid flow channel. Non-human, anti-human IgG and IgM antibodies are exemplified as goat, anti-human antibodies, however the non-human portion of the antibody can be any mammal, including but not limited to mouse, rabbit, rat, sheep, etc.

Deposited on the capture zone downstream of the label zone in a channel of the exemplary test strip for detecting or staging Lyme disease is an antigen for a species in the *Borrelia* genus. For example, for detecting or staging Lyme infection due to *B. burgdorferi*, one or more peptide antigens from *B. burgdorferi* is deposited on the test lines (capture zones) in each of the flow paths on the test strip. In one example, peptide antigens with binding affinity to the OspC, C6 or BBK07 regions of *B. Burgdorferi* are deposited in an immobile fashion to the capture zone. Examples of peptide antigens are known in art, such as in U.S. Pat. Nos. 8,338, 556; 6,716,574; 6,719,983; 8,071,109; 8,354,240; 6,475, 492; 6,660,274; 7,887,815; 2015/0017666 and Ser. No. 15/247,633, which are each incorporated by reference herein. In one embodiment, the peptide antigen deposited in a capture zone binds the C6 region of *B. burgdorferi*. In other embodiments, the peptide antigen deposited in at least one capture zone is a peptide antigen that binds the C6 region and is attached to the capture zone with a biotin-streptavidin interaction.

In one embodiment, a test strip with a plurality of peptides immobilized in each capture zone in each of the fluid flow paths or mobilizable on the label zone in each of the fluid flow paths is provided. The plurality of peptides can be the same or different in each of the capture zones and/or label zones. In one embodiment, the plurality of peptides comprises 3 or more, or 4 or more, or 5 or more, or 6 or more, or 7 or more, or 8 or more, different peptide sequences from a *Borellia* species, such as *B. burgdorferi sensu lato*. In another embodiment, the plurality of peptides comprises more than 2 but 10 or fewer, or more than 2 but 9 or fewer, or more than 2 but 8 or fewer, or more than 2 but 7 or fewer, or more than 2 but 6 or fewer, or more than 2 but 5 or fewer, or more than 2 but 4 or fewer, different peptide that can bind specifically to an antibody against a pathogenic *Borellia* species, such as *B. burgdorferi sensu lato*. In one embodiment, the peptides are any combination of peptides with binding to OppA, Bbk32, OspC-typeK, RecA, BmpA, OspF, DbpA, ErpP, p35, OspF, CRASP 2, FlilB, p66, OspC-typeA, or DdpB. In another embodiment, the plurality of peptide antigens includes a peptide that comprises an epitope from *Borrelia* flagellin p41 and/or an epitope from *Borrelia* OspC, including active (i.e., those that specifically bind) variants thereof. Alternatively, or in addition, the plurality of peptide antigens includes a peptide that comprises an epitope from the VLsE (region IR6) *Borrelia* protein, or a shorter peptide from this region, such as a peptide with 12-18 contiguous resides from this region.

In addition to the test strip described above for detection and differentiation of IgG and IgM immunoglobulins against a pathogenic *Borrelia* species, test devices that detect and differentiate or discriminate herpes simplex virus-1 and herpes simplex virus-2 (HSV-1 and HSV-2), influenza A and influenza B (Flu A and Flu B), influenza A+B and respiratory syncytial virus (RSV), and human metapneumovirus (hMPV) are contemplated. As can be appreciated, the multichannel test strip with a plurality of fluid flow paths communicating from a common sample reservoir provide an approach to differentiating a plurality of analytes of interest from a sample placed on the common sample reservoir.

With regard to a test strip or device for detection and differentiation of HSV-1 and HSV-2, a test strip is contemplated that is comprised of a first label zone and a second label zone each comprising a mobilizable, detectable anti-human IgG antibody. The first test zone comprises an immobilized antigen with binding affinity for HSV-1 and the second test zone comprises an immobilized antigen with binding affinity for HSV-2. An optional reference zone may be positioned downstream of the first test zone and comprises a binding member of a binding pair independent from the HSV infectious pathogen or comprises a non-human antibody that binds the mobilizable, detectable anti-human IgG antibody deposited on the label zones. It will be appreciated that the label zone, capture zone and/or reference zone can comprise an m×n array of drops of reagent comprising the noted species.

With regard to a test device for detection and differentiation of Flu A and Flu B, a test strip is contemplated that is comprised of a first fluid flow channel with an associated label zone with a mobilizable, detectable anti-flu A nucleoprotein antibody and a second fluid flow channel with an associated label zone with a mobilizable, detectable anti-flu B nucleoprotein antibody. A test zone in each channel is positioned downstream of the label zone in each channel and comprises, respectively, an immobilized anti-flu A nucleoprotein antibody and an immobilized anti-flu B nucleoprotein antibody. If present, a reference zone is in another channel or is downstream of a test line and comprises a binding member of a binding pair independent from the Flu A, Flu B infectious pathogen or comprises a non-human antibody that binds the mobilizable, detectable anti-flu A (or flu B) nucleoprotein antibody deposited on the label zone (array). It will be appreciated that the label zone, capture zone and/or reference zone can comprise an m×n array of drops of reagent comprising the notes species.

With regard to a test device for detection and differentiation of Flu A, Flu B, RSV and/or hMPV, a test strip is contemplated that is comprised of a label arrays in discrete fluid flow channels, the array in each channel having reagents for detection of one of the infections species. For example, a first fluid flow channel comprises a label zone with a mobilizable, detectable anti-flu A nucleoprotein antibody; a second fluid flow channel comprises a label zone with a mobilizable, detectable anti-flu B nucleoprotein antibody; a third fluid flow channel comprises a label zone with a mobilizable, detectable anti-RSV antibody; and a fourth fluid flow channel comprises a label zone with a mobilizable, detectable anti-hMPV antibody. The label zone can be an array of dots comprising the mobilizable, detectable antibody. Each channel also comprises a capture zone with an immobilized species that binds the mobilizable, detectable antibody in the upstream label zone. If present, a reference array is in another channel or is downstream of a test array and comprises a binding member of a binding pair independent from the infectious pathogens or interest or comprises a non-human antibody that binds the mobilizable, detectable antibody deposited on a label array. It will be appreciated that the label zone, capture zone and/or reference zone can comprise an m×n array of drops of reagent comprising the noted species, where m and n have any of the values described above.

In other embodiments, a test strip having a substrate with laser-etched features is created for use in detecting the presence or absence of procalcitonin, human chorionic gonadotropin hormone, anti-interleukin-23, and *Streptococcus pyogenes* are contemplated. A test strip for allergy testing or allergy screening is also contemplated, and a non-limiting example includes a test strip for detecting IgE and IgG. In one embodiment, the test strip is designed for instrument reading and is not intended to be visually read by the human eye.

Figure 20C:
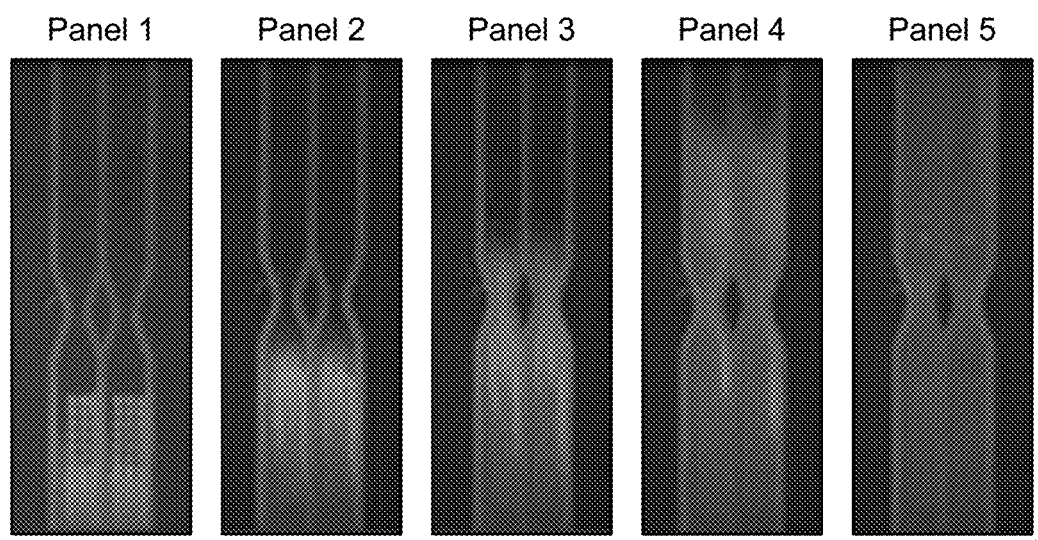
FIG. 20C are images taken over a 5 minute period of a conjugate zone and a capture zone of a test strip for detection of Group A Streptococcal antigen, where Panel 1 and Panel 2 show the sample fluid front as it encounters the conjugate zone, Panel 3 shows the fluid front as it traverses the fluid control feature, and Panel 4 and Panel 5 show the sample fluid front in the capture zone.

Example 2 details another exemplary test strip intended for detection of an infectious agent, such as *Streptococcus pyogenes*. Test strips like that shown in FIG. 20A were fabricated to have a conjugate zone and a capture zone, each zone having an array of discrete dots composed of a reagent with a binding member. As described in Example 2, a reagent comprising an antibody for an infectious agent, in this example an anti-Strep A antibody that binds to *Streptococcus pyogenes* (Group A *streptococcus*) with an attached detectable label was dispensed in the conjugate zone in a 3×12 dot array, as seen best in FIG. 20C, Panel 1. A reagent comprising a second anti-Strep A antibody was dispensed in the capture zone in an array of 1×5 discrete dots. Sample spiked positive for Streptococcal Group A was added to the sample receiving zone, and images of the test strip were taken as the sample fluid front travelled across the conjugate zone (FIG. 20C, Panel 1, Panel 2), across the fluid control feature (FIG. 20C, Panel 3), and across the capture zone (FIG. 20C, Panel 4, Panel 5). The image shown in Panel 5 of FIG. 20C was taken 5 minutes after sample was deposited in the sample receiving zone.

It will be appreciated that the multichannel device described herein can be constructed to detect the presence or absence of all the above analytes in a single device.

Accordingly, the test strip or device herein is designed to determine presence of infection due to an infectious agent, and is able to detect and discriminate a plurality of analytes in a biological sample that are indicative of the infectious agent. The device or test strip comprises a sample receiving zone configured to receive a liquid sample from a subject suspected of having an infection due to an infectious agent, the sample receiving zone positioned to distribute the sample to a plurality of fluid flow channels, where each channel has a discrete fluid flow path comprising a label zone and a capture zone. Each label zone comprises an array composed of drops of reagent comprising mobilizable, detectable species able to bind distinct antibodies against the infectious agent. Each capture zone comprises an array composed of drops of reagent comprising an immobilized species with binding affinity for the mobilizable detectable species in the label zone upstream in the same fluid flow path.

In one embodiment, the volume of fluid sample deposited on the device is less than about 100 preferably less than 75 preferably less than 50 preferably between 10-75 preferably between 10-60 µL and preferably between 10-50 µL.

In another embodiment, the test yields a detectable signal at the first and/or second test arrays within about 20 minutes or less after depositing the fluid sample, or within about 15 minutes or less after depositing the fluid sample, or within about 10 minutes or less after depositing the fluid sample, or between about 10-30 minutes after depositing the fluid sample, or between about 10-45 minutes after depositing the fluid sample.

IV. Examples

The following examples are illustrative in nature and are in no way intended to be limiting.

Example 1

Substrate with Fluid Flow Channel and Fluid Control Feature

A nitrocellulose membrane (HF 120 from Millipore, Inc.) having a length of approximately 30 centimeters and a width of approximately 2.5 centimeters is laminated onto a base layer (or support layer) of polyethyleneteraphthalate. A fluid flow channel is formed on the nitrocellulose membrane using a carbon dioxide ($CO_2$) laser by ablating nitrocellulose to form parallel side walls. The resulting fluid flow channel had a depth of approximately 0.2 millimeters and a length of 2 millimeters. A fluid control feature is patterned onto the fluid flow channel using the $CO_2$ laser.

Example 2

Test Strip with a Substrate with Laser-Etched Fluid Flow Channels and Fluid Control Features for Detection of *Streptococcus pyogenes*

An assay test strip for detection of *Streptococcus pyogenes* was prepared. Test strips as illustrated in FIG. 20A were fabricated to have a conjugate zone and a capture zone, each zone having an array of discrete dots composed of a reagent with a binding member. A reagent comprising a rabbit polyclonal anti-Strep A antibody that binds to *Streptococcus pyogenes* (Group A *streptococcus*) with an attached detectable label was dispensed in the conjugate zone in a 3×12 dot array. A reagent comprising a second rabbit polyclonal anti-Strep A antibody was dispensed in the capture zone in an array of 1×5 discrete dots. Sample (30 uL) spiked positive for Streptococcal Group A was added to the sample receiving zone, and images of the test strip were taken as the sample fluid front travelled across the conjugate zone (FIG. 20C, Panel 1, Panel 2), across the fluid control feature (FIG. 20C, Panel 3), and across the capture zone (FIG. 20C, Panel 4, Panel 5). The image shown in Panel 5 of FIG. 20C was taken 5 minutes after sample was deposited in the sample receiving zone.

Example 3

Comparison of Direct Cast and Adhesive Backed Substrates

Figure 21A:
FIGS. 21A-21B provide a photograph of sample droplets on nitrocellulose substrates with direct cast hydrophobic backing (21A) and adhesive backed hydrophobic backing (21B).
Figure 21B:
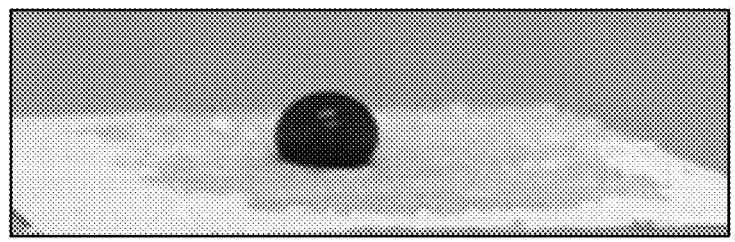

In this experiment, the fluidic behavior of a 2% dye in phosphate buffered saline aqueous solution was assessed on nitrocellulose laminates having different backing materials. A first material was prepared from nitrocellulose that was directly cast onto a hydrophobic backing. A portion of nitrocellulose substrate was scratched away from the backing to form a circular nitrocellulose structure that simulates a sample receiving zone. A 10 μL aliquot of dye solution was placed on the structure. FIG. 21A provides a photograph of the sample droplet on the direct cast substrate. It can be seen that the hydrophobic backing prevents the droplet from spreading, and the droplet has an ellipsoidal shape. A second material was prepared from a nitrocellulose substrate attached to a hydrophobic backing by an adhesive. A circular nitrocellulose structure was formed by scratching off a portion of the nitrocellulose, and a 10 μL aliquot of dye solution was placed thereon. FIG. 21B provides a photograph of the sample droplet on the adhesive backed nitrocellulose substrate, which shows a steep contact angle and a nearly spherical shape. This steeper contact angle and spherical shape are indications that the adhesive in the backing provides an extra degree of hydrophobicity.

Example 4

Effect of Hydrophobic and Hydrophilic Backing

Figure 22A:
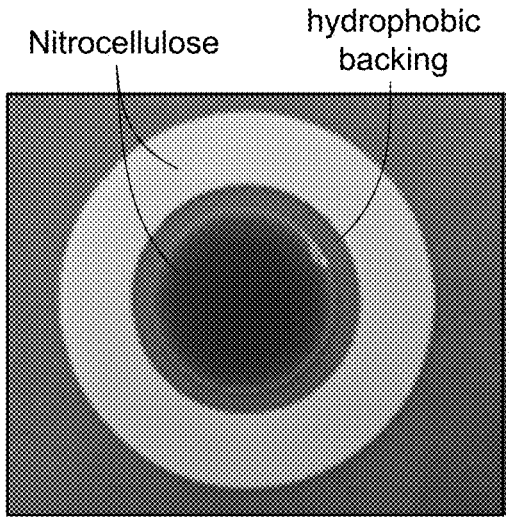
FIGS. 22A-22D are photographs of sample droplets placed on nitrocellulose substrates with different backings.
Figure 22C:
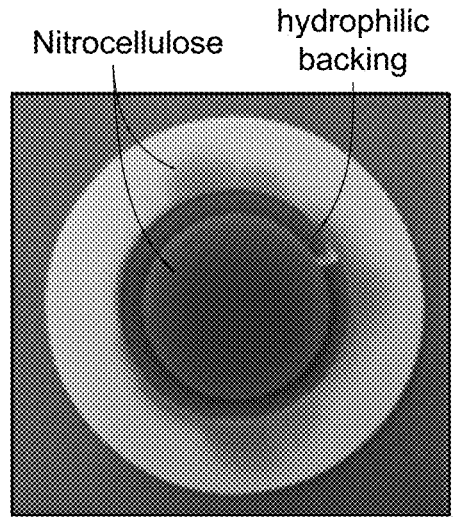
Figure 22B:
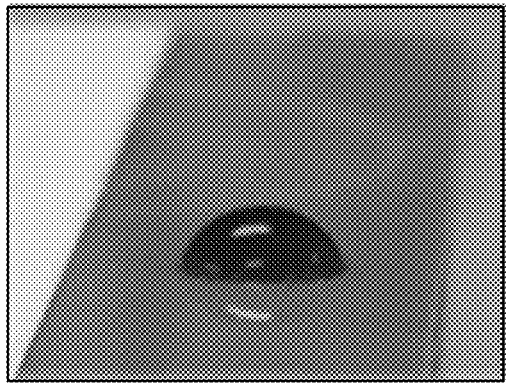
Figure 22D:
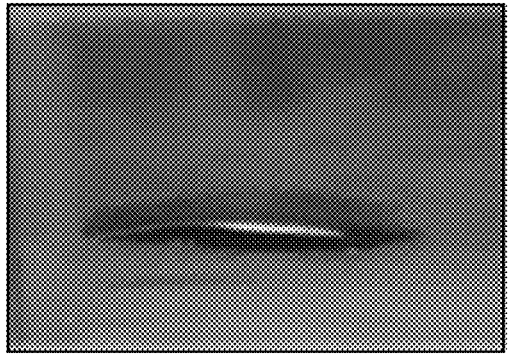

In this experiment, the fluidic behavior of a 2% dye in phosphate buffered saline aqueous solution was assessed on nitrocellulose substrates with different backings. The substrates were prepared from unbacked nitrocellulose, which was lasered to prepare an inner circular structure, simulating a sample receiving zone, and outer ring. The inner circle was 10 mm in diameter, and the outer ring was concentric to the inner circular nitrocellulose with a 1 mm gap, which was designed to mimic a fluidic barrier (without adhesive). Substrates were then placed on either a hydrophobic backing or a hydrophilic backing, and 30 μL aliquots of the 2% dye solution were placed onto the inner circles of the substrates. The results of this experiment can be seen in the photographs of FIGS. 22A-22D. FIG. 22A shows an image taken directly above a sample droplet placed on a substrate with a hydrophobic backing, and FIG. 22B shows a lateral view of the same. It can be seen that the droplet is contained on the circular structure and does not flood or seep into the fluidic barrier. Moreover, the droplet has a highly spherical shape with a steep contact angle. In contrast, FIG. 22C shows an image taken directly above a sample droplet placed on a substrate with a hydrophilic backing, and FIG. 22D shows a lateral view of the same. It can be seen that the droplet is not contained on the circular structure and floods into the gap and to the outer ring. With respect to the sample dye solution, which is aqueous, the hydrophilic backing is too wettable to contain sample within the nitrocellulose circle in the center, the sample flows along the gap, absent of nitrocellulose, and continues to wet the outer nitrocellulose circle.

Figure 23:
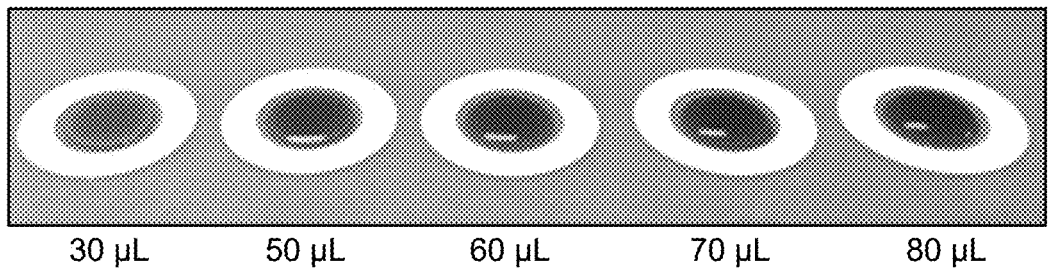
FIG. 23 provides a photograph of sample droplets of varying volume placed on nitrocellulose substrates with a hydrophobic backing.

In addition to the above experiment, the concentric circular hydrophobic backing was further challenged with sample volumes of 30, 50, 60, 70, and 80 μL without any observable wicking. The results can be seen in FIG. 23. In agreement with the results shown in FIG. 22A, samples were contained within the center circular nitrocellulose in all cases.

In this experiment, the hydrophobic property of a nitrocellulose backing is shown to be a factor that contributes to sample containment and fluidic control, independent of whether adhesive is present. In addition, it is shown that fluidic control can be achieved by controlling the properties of the nitrocellulose, the properties of the backing, and/or the properties of the test fluid. In order to achieve a robust fluidic structure capable of handling a vast array of sample types, controlling the backing property seems to be the most appropriate choice. When using polar fluids such as water-based samples, the nitrocellulose should be more hydrophilic than the backing in order to direct the sample flow through the nitrocellulose pores. Conversely, if the backing is more hydrophilic than the nitrocellulose, then the sample would favor the higher surface energy of the hydrophilic backing.

Example 5

Test of Running Buffer

A running buffer was developed containing 5 wt % sucrose, 2 wt % bovine serum albumin (BSA), and 1 wt % TWEEN®-20 (Tw-20) in a 10 mM borate buffer of pH 8.5. This buffer and each of its components were assessed for their respective effects upon the migration of sample analyte along a flow path.

Sample test strips employed in this assessment had a spherical sample receiving zone, a conjugate zone, and a capture zone. The conjugate zone and the capture zones consisted of five separate flow channels. The conjugate zone was connected to the sample receiving zone and a fluid control feature was placed there between consisting of diamond-shaped structures etched upon the substrate. Likewise, the conjugate zone is separated from the capture zone by diamond-shaped fluid control features. Each capture flow channel had four capture drops containing a goat anti-mouse antibody (GAMG) deposited in succession thereon and thereby forming an array.

Aliquots of running buffer containing 0.0025 wt. % test analyte were placed on the sample receiving zones and allowed to elute until completion (i.e., fluid reached the top of the capture zone). The test analyte was a europium particle (330 nm) conjugated to a human Chorionic Gonadotropin (hCG) mouse antibody. Migration of the test analyte was detected by fluorescence of the europium particles.

Figure 24:
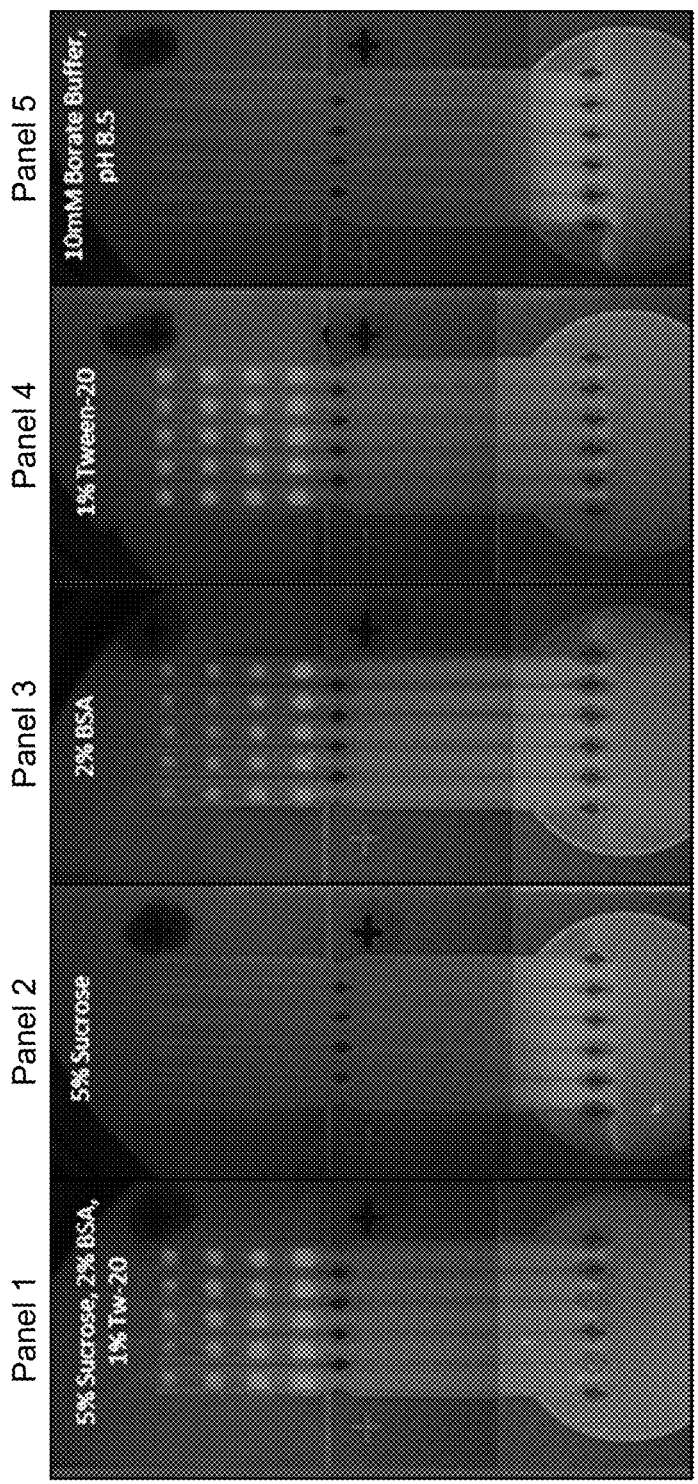
FIG. 24 provides images taken after flow of a particle analyte in various buffers along exemplary test strips having a capture zone, where Panel 1 shows the results of an exemplary running buffer, Panel 2 shows the results of a buffer of 5% sucrose, Panel 3 shows results in a buffer of 2% bovine serum albumin (BSA), Panel 4 shows results in a buffer of 1% Tween-20, and Panel 5 shows results in 10 mM, pH 8.5 borate buffer.

FIG. 24 provides images taken after flow completion of the particle analyte, where Panel 1 shows the results of the running buffer, Panel 2 shows the results of a buffer of 5% sucrose, Panel 3 shows results in a buffer of 2% bovine serum albumin (BSA), Panel 4 shows results in a buffer of 1% Tween-20, and Panel 5 shows results in 10 mM, pH 8.5 borate buffer. Panel 1 shows strong fluorescence at the capture array, with minimal amount of fluorescence at the sample receiving zone, showing that the running buffer functions to carry the analyte along the flowpath until it is immobilized at the capture zone. Likewise, Panels 3 and 4 show a similar fluorescence pattern, indicating that BSA and Tween-20 are the primary components of the running buffer that function in carrying the analyte. In contrast, fluorescence in Panels 2 and 5 is largely concentrated near the sample receiving zone, indicating that sucrose and borate buffer are insufficient for carrying the analyte to the capture zone.

Figure 25:
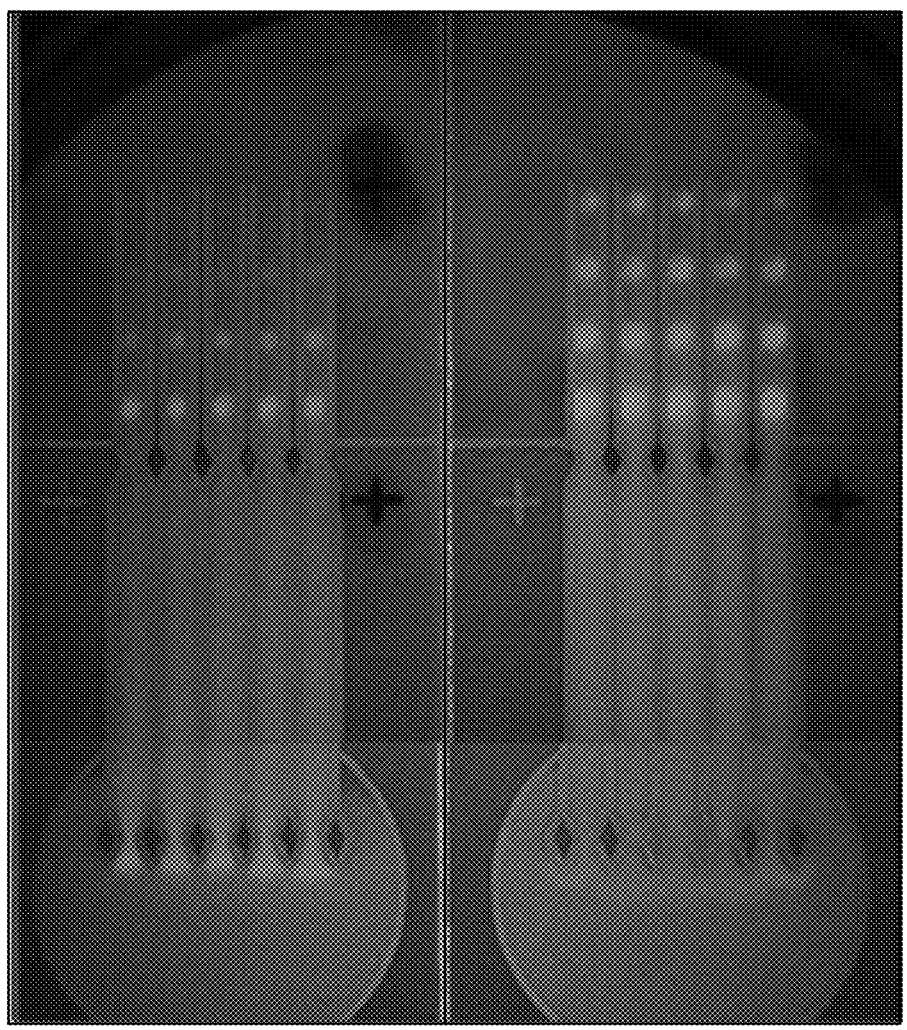
FIG. 25 provides images taken after flow of a particle analyte in a serum sample (Panel 1) in comparison to a solution of a particle analyte in an exemplary running buffer (Panel 2).

A further experiment was conducted to compare the running buffer to elution of a serum sample. FIG. 25 provides images taken after flow of a particle analyte in serum (Panel 1) in comparison to a solution of a particle analyte in running buffer (Panel 2). The serum sample shows a small amount of fluorescence in the capture zone and some fluorescence in the sample receiving zone indicating that the serum sample is not as effective as the running buffer in carrying the sample analyte.

Example 6

Effect of Prewetting and Chasing with Additional Buffer

Figure 26:
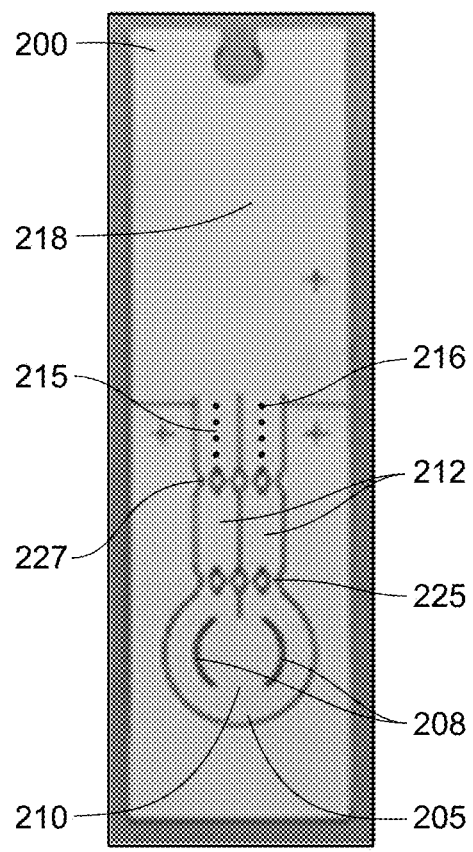
FIG. 26 shows an exemplary strip according to some embodiments, where the strip comprises a sample receiving zone separated from a conjugate pathway by a fluid control feature (diamonds), which is further separated from a capture pathway by a second fluid control feature (diamonds).

A further experiment was conducted to assess the prewetting effect on analyte flow and capture. A test strip 200 was employed in this experiment as depicted in FIG. 26. In test strip 200, a circular fluid receiving zone 205 has fluid control features 208, which form opposing circular arcs with gaps 210 therebetween. Extending from fluid receiving zone 205 are fluid channels 212, which are separated from the fluid receiving zone 205 by fluid control features 225. Extending from fluid channels 212 at an end distal to the fluid receiving zone 205 is a capture zone 215. Capture zone 215 contains an array of immobilized capture spots 216. In the present experiment, the capture spots 216 contain GAMG. The capture zone 215 is separated from fluid channels 212 by a second fluid control feature 227. At an end opposite from fluid control feature 227, the capture zone is connected to a destination zone 218, which allows for a running buffer to flow ahead of the capture zone.

Figure 27:
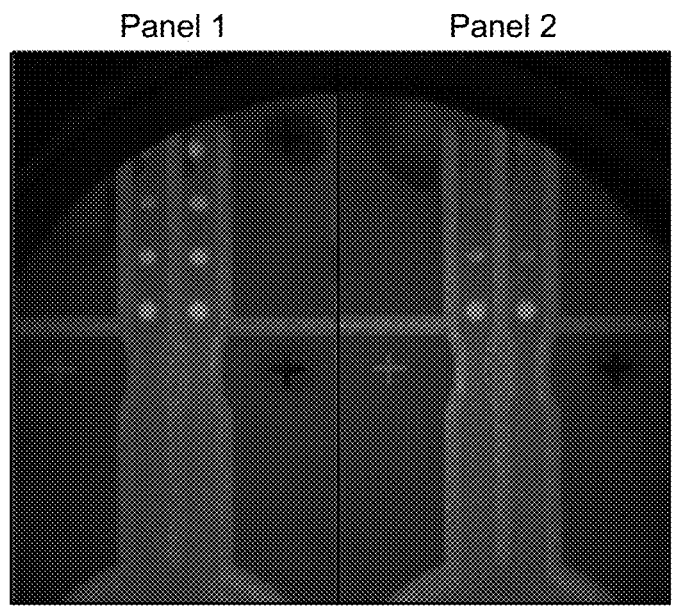
FIG. 27 provides images taken after flow of a particle analyte in exemplary running buffer on a test strip of FIG. 26, where Panel 1 shows the results of a strip that was prewet with 25 µL of buffer and Panel 2 shows the results of a strip that was not prewet.

A first strip was prewet with 25 µL of running buffer as described in Example 5, which was allowed to flow to completion. 25 µL aliquots of running buffer with 0.001% europium particles (330 nm) conjugated to hCG mouse antibody were then added to both the prewet and a dry test strip. The results are shown in FIG. 27, where Panel 1 shows the results of a strip that was prewet with 25 µL of buffer and Panel 2 shows the results of a strip that was not prewet. The prewet strip shows fluorescence in all four of the capture spots while the strip that was not prewet shows bright fluorescence in the first capture spot, mild fluorescence in the second spot, and hardly any signal in the third and fourth spots.

Figure 28:
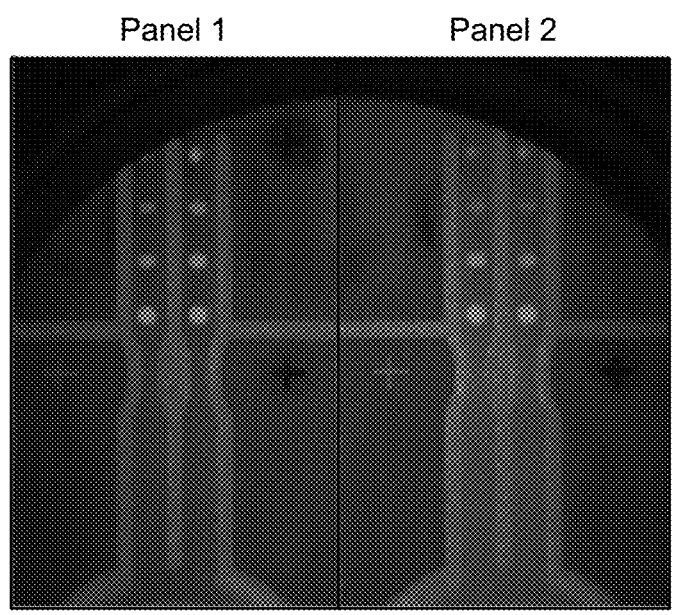
FIG. 28 provides images taken after flow of a particle analyte in exemplary running buffer on an exemplary test strip of FIG. 26, where Panel 1 shows the results of a strip that was prewet with 25 µL of buffer and Panel 2 shows the results of a strip that was not prewet, but was chased with an additional 25 µL of buffer after flow of the sample.

The non-prewet strip was subsequently chased with an additional 25 µL of buffer, and the results can be seen in FIG. 28, where Panel 1 shows the prewet strip that has not been chased and Panel 2 shows the results of the non-prewet strip after chasing with the additional buffer. It can be seen that chasing with additional buffer improves the signal output and sample flow of the analyte. The prewet technique or chasing technique can be beneficial in assays having multiple capture dot arrays to ensure adequate sample analyte capture. For example, the method could be employed in a serological assay, in which a plasma or serum sample is flowed to completion and subsequently chased with a buffer comprising a reporter agent.

Example 7

The Effect of Funnel Width in a Fluid Control Feature

Figure 29:
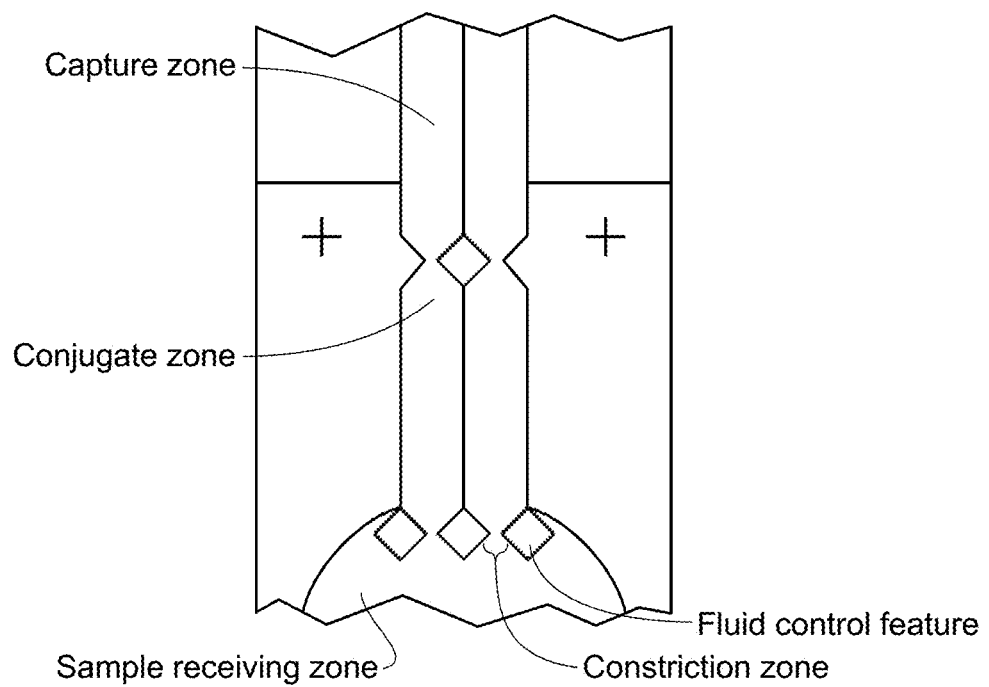
FIG. 29 shows an exemplary strip according to some embodiments, where the strip comprises a sample receiving zone, a conjugate zone, and a capture zone. The sample receiving zone is separated from the conjugate zone by a diamond-shaped fluid control feature of three diamond-shaped barriers spaced apart by a constriction zone or funnel which can be defined by a funnel width, which is the distance between two of the diamond-shaped barriers. A second fluid control feature of this configuration is placed between the conjugate zone and the capture zone.

Test strips were designed and experiments were conducted to assess the effect of the fluid control feature on the flow rate and flow time of the fluid sample. An exemplary test strip design is depicted in FIG. 29, in which the strip comprises a sample receiving zone, a conjugate zone, and a capture zone. The sample receiving zone is separated from the conjugate zone by a diamond-shaped fluid control feature of three diamond-shaped barriers spaced apart by a constriction zone or funnel, which can be defined by a funnel width, or the distance between two of the diamond-shaped barriers. A second fluid control feature of this configuration is placed between the conjugate zone and the capture zone.

Figure 30A:
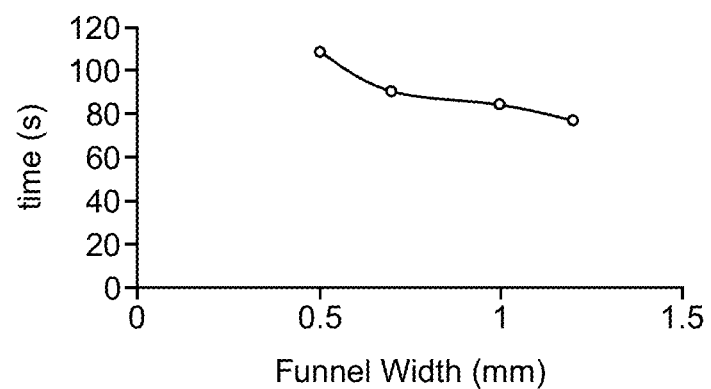
FIGS. 30A-30B provide graphs showing the results of experiments testing the effects of the funnel width of a diamond-shaped fluid control feature as exemplified in FIG. 29, where
Figure 30B:
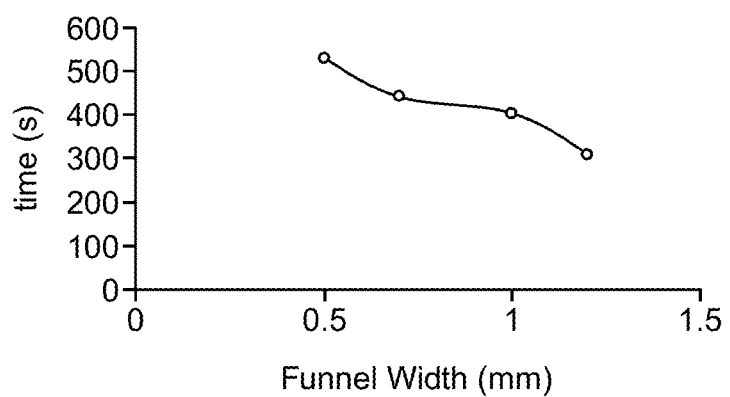

Four strips were prepared according to the design depicted in FIG. 29 with varying funnel widths of 0.5 mm, 0.7 mm, 1.0 mm, and 1.2 mm. An aliquot of 50 µl of a 2% green dye solution diluted in phosphate buffer saline was added to each strip, and the time for each fluid to reach the top of the capture zone (capture time) and the time for the fluid to fully elute (completion time) were measured. FIG. 30A shows a graph of the Funnel Width versus Capture Time and FIG. 30B shows a graph of the Funnel Width versus Completion Time. In both cases, the capture time and the completion time decrease with increasing funnel width. The optimal time to conduct an assay can vary depending on the specific test performed and the environment, but the results of this experiment show that the flow rate and time for completion of an assay can be controlled by selecting the funnel width in a fluid control feature.

Example 8

Effect of Capture Path Length

Figure 31:
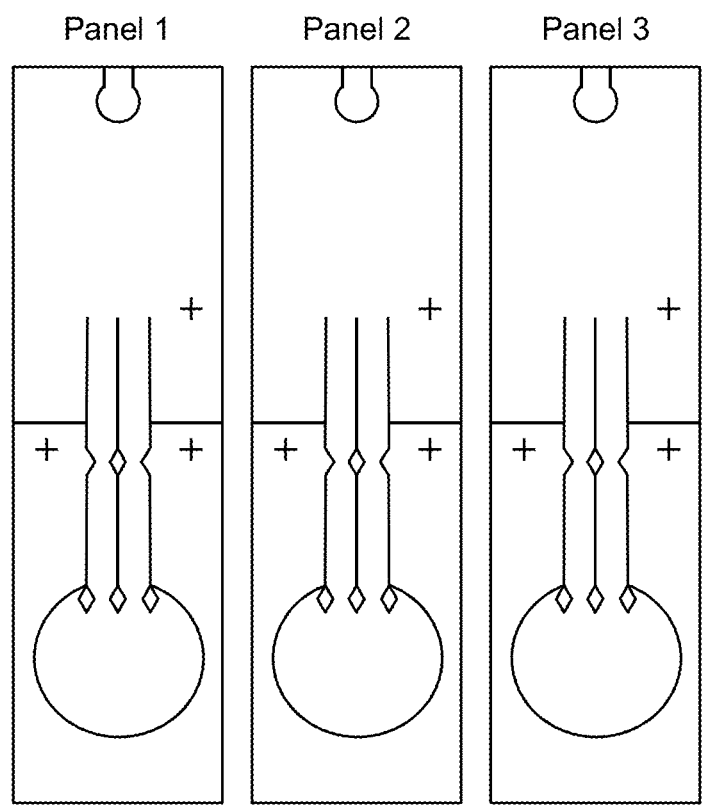
FIG. 31 shows exemplary test strips with varying capture pathlength designs, where Panel 1 has a capture pathlength of 10 mm, Panel 2 has a capture pathlength of 8 mm, and Panel 3 has a capture pathlength of 5 mm.
Figure 32:
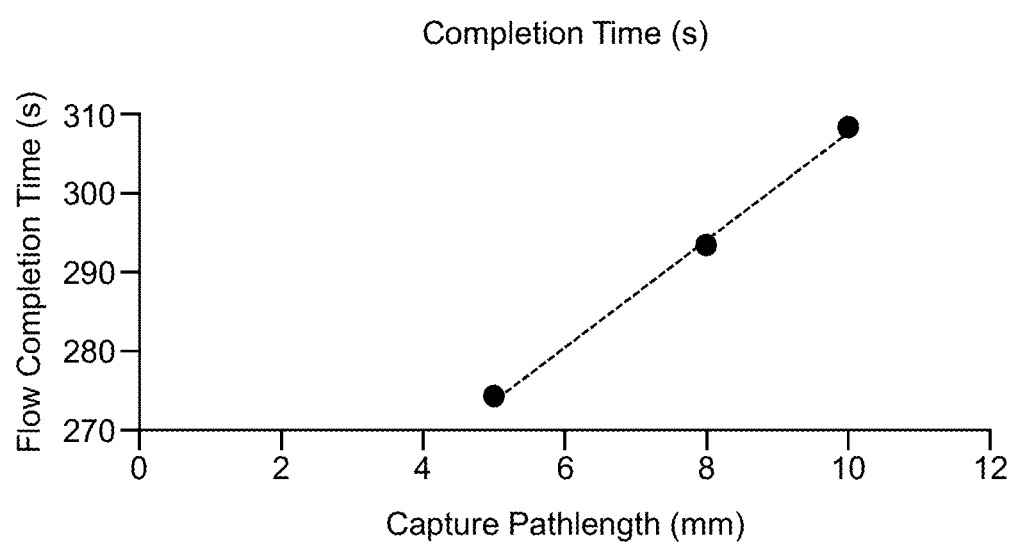
FIG. 32 provides a graph showing the effect of capture pathlength on completion time in test strips having the configurations exemplified in FIG. 31.

Test strips were designed and experiments were conducted to assess the effect of capture path length on completion time. FIG. 31 shows exemplary test strips, similar to those depicted in FIG. 29, but with varying capture path length designs, where Panel 1 has a capture path length of 10 mm, Panel 2 has a capture path length of 8 mm, and Panel 3 has a capture path length of 5 mm. 50 µl of a 2% green dye solution diluted in phosphate buffer saline was added to each strip, and the time for each fluid to completely elute from the sample zone (completion time) was measured. FIG. 32 shows a graph of the Capture Path length versus Completion Time. As with the test for funnel width, the optimal time to conduct an assay can vary depending on the specific test performed and the environment, but the results of this experiment show that the flow rate and time for completion of an assay can be controlled by selecting an appropriate capture path length.

Example 9

Control of Inter-Channel Flow Rate

Figure 33B:
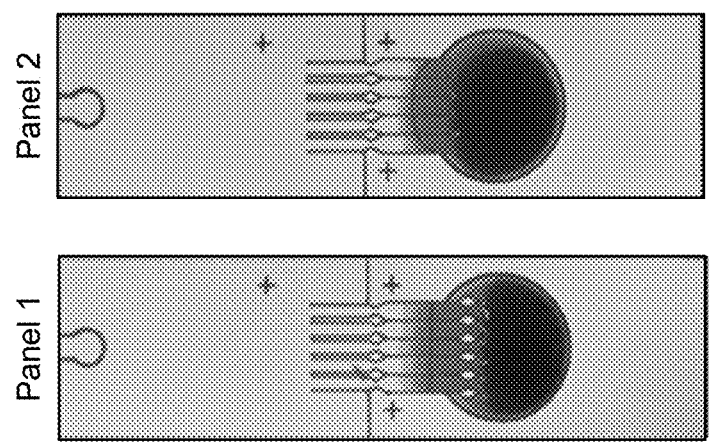
FIG. 33B is an image of an investigation of interchannel flow rate control of a 45 µL 2% green dye test solution on the test strips of FIG. 33A.
Figure 33A:
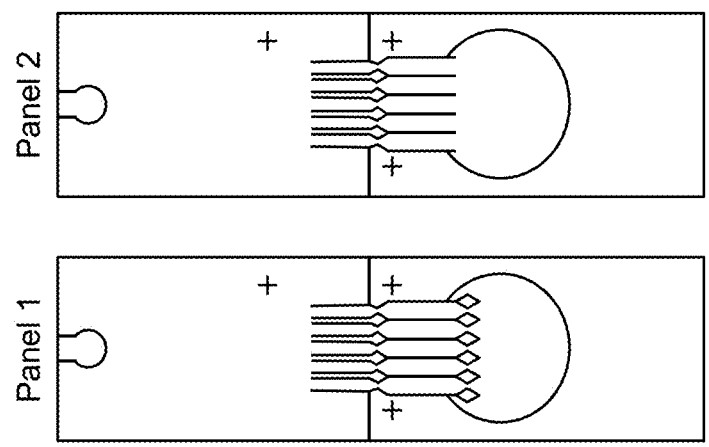
FIG. 33A depicts two test strips designed to test the effect of a fluid control feature in which Panel 1 shows a test strip having a fluid control feature in the sample receiving zone and the test strip of Panel 2 does not.

This experiment was performed to assess the effect of a fluid control feature on the comparative flow rate among channels on the same test strip (interchannel flow rate). Two test strips were designed for this experiment, each having a spherical sample receiving zone extending into five fluid channels. The five fluid channels had a first zone operably connected to the sample receiving zone at a proximal end, and a second zone that connects to the first zone at a distal end to form a linear flow path. At the junction of the first and second zones is a fluid control feature, or constriction zone, consisting of etched diamond-shaped structures. The first strip differed from the second in that a second fluid control feature was placed at the junction of the first zone of the five fluid channels and the sample receiving zone consisting of etched diamond-shaped structures with a funnel width there between. The two test strips are depicted in FIG. 33A.

Aliquots of 45 µl of a 2% dye solution in phosphate buffered saline were added to each strip, and the samples were allowed to flow into the first zone. FIG. 33B shows images of the two test strips after the samples reached the first zone. An artificial line is depicted across the fluid samples to emphasize the shape of the flow front. The strip with diamonds in the sample port showed similar flow rates and a flat flow front (emphasized by straight line) among the five channels. In contrast, the strip without diamonds in the sample port showed slower flow rates in the outer channels, and the flow front across all five channels appeared to take on the shape of the sample drop in the sample port (emphasized by curved line). The results indicate that a fluid control feature in the sample port serves to slow the influx of sample into the fluid channels as well as even out the flow rate among channels in a multi-channel strip.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. An immunoassay device, comprising:
   a substrate comprised of a plurality of parallel fluid flow channels, wherein each parallel fluid flow channel is separated from an adjacent parallel fluid flow channel by a substrate-devoid gap, and wherein the substrate-devoid gaps form side channels that are impermeable to fluid flow;
   a fluid control feature positioned in each fluid flow channel to form a plurality of fluid flow control features ablated or etched on the substrate;
   a single sample receiving zone positioned on the substrate to distribute a portion of a sample deposited thereon to each fluid flow channel in the plurality of parallel fluid flow channels;
   a label zone in each of the fluid flow channels; and
   a capture zone downstream of the label zone in each of the fluid flow channels,
   wherein the label zone, the capture zone, or both the label zone and the capture zone comprise a reagent comprising a binding member.

2. The device of claim 1, wherein the plurality of fluid flow channels comprises between 3-50 fluid flow channels.

3. The device of claim 1, wherein the sample receiving zone dispenses sample to each channel in essentially equal amounts and at essentially equal rates.

4. The device of claim 1, wherein the substrate comprises a laminate of nitrocellulose and a hydrophobic support layer.

5. The device of claim 1, wherein the binding member in the capture zone in each of the plurality of parallel fluid flow channels is an immobilized binding member that binds a conjugate, wherein the conjugate is comprised of a detectable species and an antibody.

6. The device claim 5, wherein the detectable species is an antibody with a label.

7. The device of claim 6, wherein the label is a fluorescent or chemiluminescent marker.

8. The device of claim 5, wherein the detectable species is a europium bead.

9. The device of claim 1, wherein each fluid control feature in the plurality of fluid control features is in a flow rate control zone disposed downstream of the sample receiving zone.

10. The device of claim 9, wherein the flow rate control zone is disposed between the sample receiving zone and the label zone.

11. The device claim 1, wherein the substrate comprises nitrocellulose.

* * * * *